(12) United States Patent
Zweber et al.

(10) Patent No.: US 11,357,993 B2
(45) Date of Patent: *Jun. 14, 2022

(54) IMPLANTABLE MEDICAL LEAD WITH MOVEABLE CONDUCTORS

(71) Applicant: Medtronic, Inc., Minneapolis, MN (US)

(72) Inventors: Jeffrey Zweber, Blaine, MN (US); Joseph Bradley, Robbinsdale, MN (US); Vincent Whelan, New Brighton, MN (US); Ian Johnson, Minneapolis, MN (US); Sean P. Skubitz, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,232

(22) Filed: May 29, 2020

(65) Prior Publication Data

US 2020/0289831 A1    Sep. 17, 2020

Related U.S. Application Data

(63) Continuation-in-part of application No. 16/212,256, filed on Dec. 6, 2018.

(51) Int. Cl.
*A61N 1/375* (2006.01)
*H01R 13/52* (2006.01)
(Continued)

(52) U.S. Cl.
CPC ....... *A61N 1/3752* (2013.01); *H01R 13/5224* (2013.01); *H01R 24/58* (2013.01);
(Continued)

(58) Field of Classification Search
CPC .... A61N 1/05; A61N 1/0534; A61N 1/37247; A61N 1/3752; A61N 1/3605; H01R 13/5224; H01R 24/38; H01R 2201/12
See application file for complete search history.

(56) References Cited

U.S. PATENT DOCUMENTS 7,745,732 B2  6/2010  Mark et al.
8,364,281 B2  1/2013  Duncan et al.
(Continued)

FOREIGN PATENT DOCUMENTS

EP  1718361 B1  11/2006
EP  1793890 A2   6/2007
EP  2773420 A1   9/2014

OTHER PUBLICATIONS

Kim et al., "Spontaneous Lead Breakage in Implanted Spinal Cord Stimulation Systems," The Korean Journal of Pain, vol. 23, No. 1, Dec. 11, 2009, pp. 78-81.
(Continued)

*Primary Examiner* — Mallika D Fairchild
(74) *Attorney, Agent, or Firm* — Shumaker & Sieffert, P.A.

(57) ABSTRACT

A medical lead includes a lead body, an electrical connector, an electrical conductor, and a sleeve. The lead body includes a distal end and a proximal end defining a longitudinal axis of the lead body. The electrical connector is positioned near the proximal end of the lead body. The electrical conductor extends about the longitudinal axis of the lead body. The sleeve is coupled to an insulative material of the lead body and positioned around the electrical conductor. The electrical conductor is electrically coupled to the electrical connector. The sleeve is not fixed to the electrical conductor. In response to bending of the medical lead, the conductor may move within the sleeve to relieve strain created by the bending.

19 Claims, 15 Drawing Sheets

(51) Int. Cl.
*H01R 24/58* (2011.01)
*H01R 107/00* (2006.01)
*A61N 1/05* (2006.01)
*A61N 1/36* (2006.01)

(52) U.S. Cl.
CPC .......... *A61N 1/0534* (2013.01); *A61N 1/3605* (2013.01); *H01R 2107/00* (2013.01)

(56) References Cited

U.S. PATENT DOCUMENTS

| | | | | |
|---|---|---|---|---|
| 8,543,222 | B1* | 9/2013 | Sochor | A61N 1/0529 607/116 |
| 8,588,939 | B2 | 11/2013 | Conger | |
| 8,639,340 | B2* | 1/2014 | Sommer | A61N 1/3752 607/37 |
| 2001/0018607 | A1 | 8/2001 | Borgersen et al. | |
| 2005/0027338 | A1 | 2/2005 | Hill | |
| 2006/0142652 | A1 | 6/2006 | Keenan | |
| 2007/0088335 | A1* | 4/2007 | Jolly | A61N 1/0541 604/891.1 |
| 2007/0225674 | A1* | 9/2007 | Molnar | A61N 1/36067 604/503 |
| 2008/0077216 | A1 | 3/2008 | Chitre et al. | |
| 2008/0255629 | A1 | 10/2008 | Jenson et al. | |
| 2009/0259282 | A1* | 10/2009 | Williams | A61N 1/0587 607/122 |
| 2011/0004286 | A1 | 1/2011 | Olson | |
| 2011/0152991 | A1 | 6/2011 | Dadd et al. | |
| 2011/0196465 | A1 | 8/2011 | Dadd et al. | |
| 2013/0005169 | A1 | 1/2013 | Soltis et al. | |
| 2014/0135885 | A1* | 5/2014 | Foster | A61N 1/3752 607/122 |

OTHER PUBLICATIONS

Fernandez et al., "Lead Fractures in Deep Brain Stimulation During Long-TermFollow-Up," SAGE—Hindawi Access to Research, Parkinson's Disease, vol. 2010, Article ID 409356, Dec. 13, 2009, 4 pp.
U.S. Appl. No. 16/212,256, filed Dec. 6, 2018, by Zweber et al.
Non-Final Office Action from U.S. Appl. No. 16/212,256 dated Apr. 27, 2021 (17 pp).
Amendment filed on Jul. 27, 2021 in response to Non-Final Office Action from U.S. Appl. No. 16/212,256 dated Apr. 27, 2021 (10 pp).
Extended Search Report from European Application No. 21176233.1, dated Oct. 26, 2021, 6 pp.
Notice of Allowance from U.S. Appl. No. 16/212,256, dated Oct. 26, 2021, 8 pp.

* cited by examiner

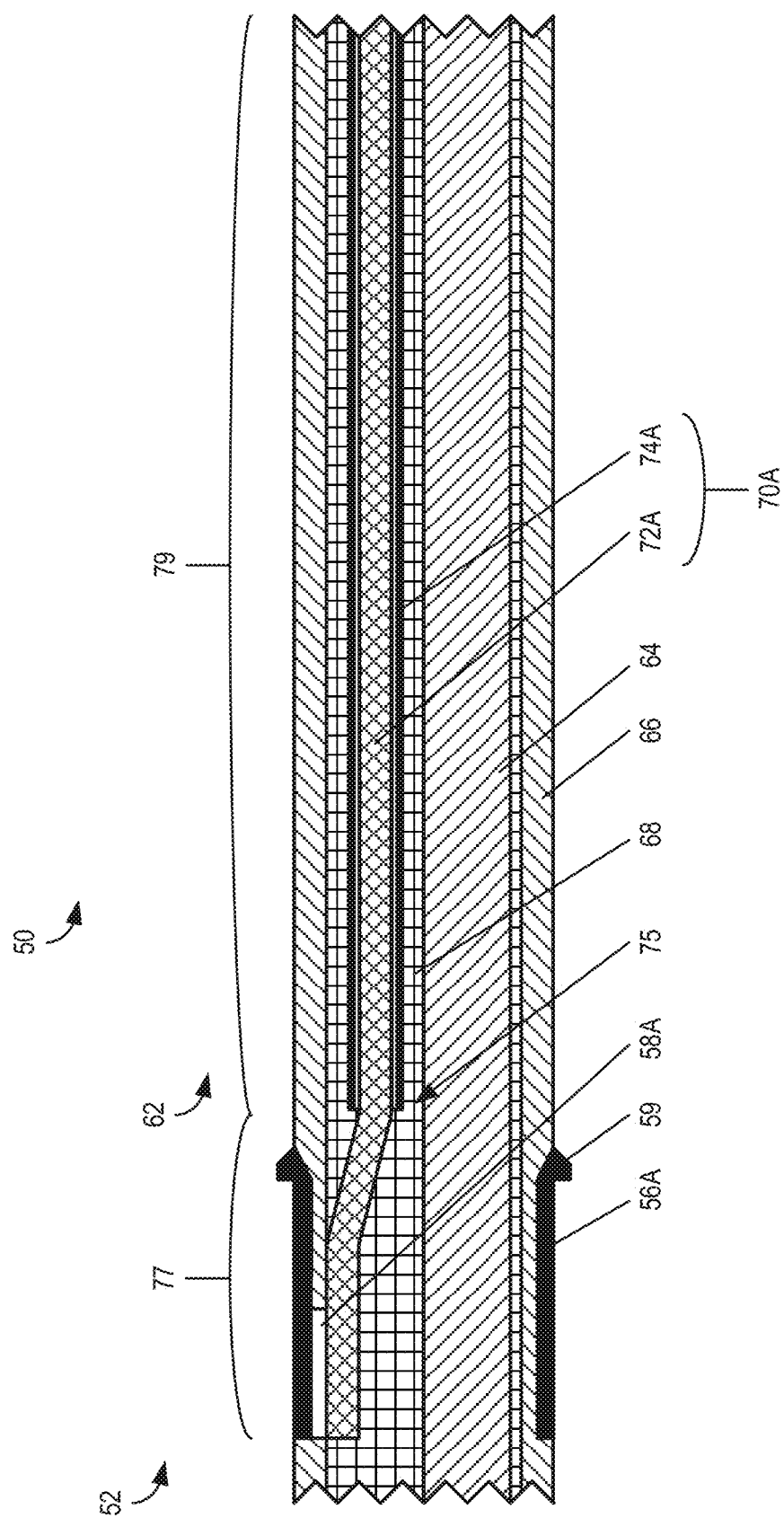

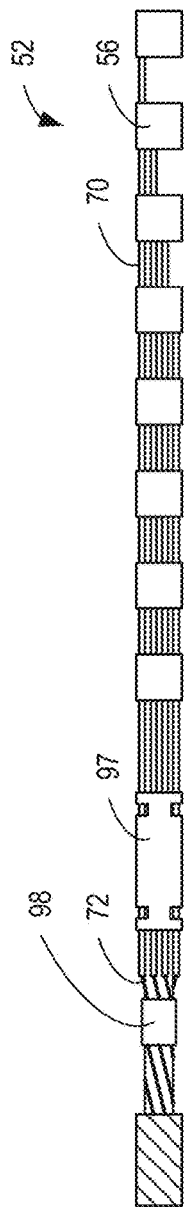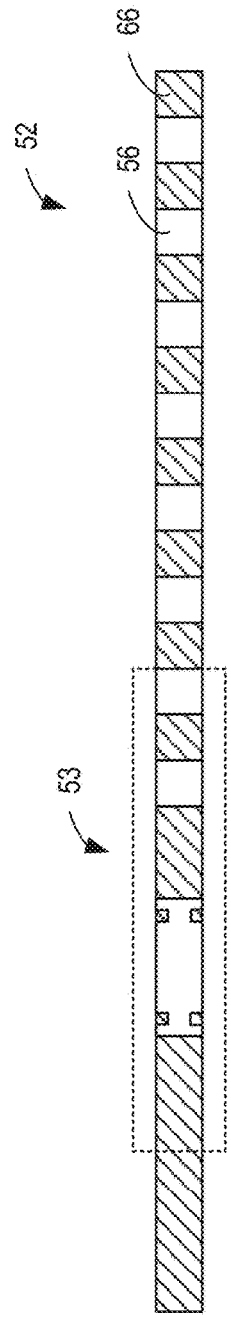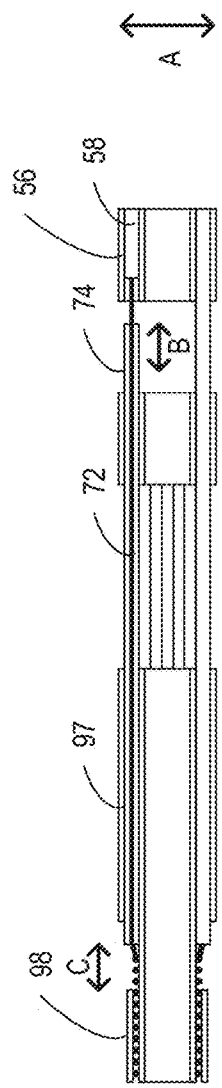
FIG. 4A
FIG. 4B
FIG. 4C

IMPLANTABLE MEDICAL LEAD WITH MOVEABLE CONDUCTORS This application is a continuation-in-part of U.S. patent application Ser. No. 16/212,256, filed on Dec. 6, 2018, entitled "IMPLANTABLE MEDICAL LEAD WITH MOVEABLE CONDUCTORS," the entire contents of which are incorporated herein by reference.

TECHNICAL FIELD

This disclosure relates to implantable medical device systems.

BACKGROUND

Medical devices may be used to deliver therapy to a patient to treat symptoms or conditions such as chronic pain, seizure disorders (e.g., epilepsy), heart arrhythmias (e.g., fibrillation), tremor, Parkinson's disease, other types of movement disorders, obesity, mood disorders, urinary or fecal incontinence, or other types of symptoms or conditions. This therapy may be electrical stimulation therapy. Medical devices, such as implantable medical devices (IMDs), may be used for therapies such as deep brain stimulation (DBS), spinal cord stimulation (SCS), sacral neuromodulation, pelvic stimulation, gastric stimulation, peripheral nerve stimulation, cardiac stimulation, functional electrical stimulation, or other types of stimulation.

SUMMARY

The disclosure describes medical device systems for delivering a therapy to a patient. For example, an implantable medical device may be configured to deliver electrical stimulation and/or sense electrical signals of a patient including a medical lead having one or more electrodes. The one or more electrodes may be electrically coupled to electrical circuitry of the implantable medical device by one or more conductors within the medical lead and/or medical lead extension. These medical leads and/or medical lead extensions may be routed through a body of a patient, such that the medical leads and/or medical lead extensions may be subject to stresses created by bends in the medical leads and/or medical lead extensions.

In some examples, a medical lead and/or medical lead extension may include one or more stress-relieving portions for conductors within the lead. In these stress-relieving portions, the conductors of the lead are not fixed to a lead body; instead, the conductors in these portions are free to move relative to the lead body in response to compressive or tensile stresses caused by bends or other movement of the lead. This relative movement may enable the lead to relieve compressive or tensile stresses for a reduced likelihood of fracture.

In some examples, the disclosure describes a medical lead system that includes a lead body, an electrical connector, an electrical conductor, and a sleeve. The lead body includes a distal end and a proximal end defining a longitudinal axis of the lead body. The electrical connector is positioned near the proximal end of the lead body. The electrical conductor extends about the longitudinal axis of the lead body. The sleeve is coupled to an insulative material of the lead body and positioned around the electrical conductor. The electrical conductor is electrically coupled to the electrical connector. The sleeve is not fixed to the electrical conductor.

In some examples, the disclosure describes a method manufacturing an implantable medical lead that includes positioning a conductor assembly in a channel extending about a longitudinal axis of a lead body and filling the channel with an insulative material. The insulative material surrounds an outer surface of the conductor assembly. The lead body includes a distal end and a proximal end defining the longitudinal axis of the lead body. The conductor assembly includes an electrical conductor and a sleeve positioned around the electrical conductor. The sleeve forms the outer surface of the conductor assembly and is not fixed to the electrical conductor.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIG. 3E is a conceptual diagram illustrating a longitudinal cross-sectional view of an example medical lead.

FIG. 4A is a conceptual diagram illustrating a side view of proximal end of a lead without insulative material and a jacket.

FIG. 4B is a conceptual diagram illustrating a side view of proximal end of a lead with insulative material and jacket.

FIG. 4C is a cross-sectional side view diagram of a section of a proximal end of an example medical lead.

DETAILED DESCRIPTION

Figure 1:
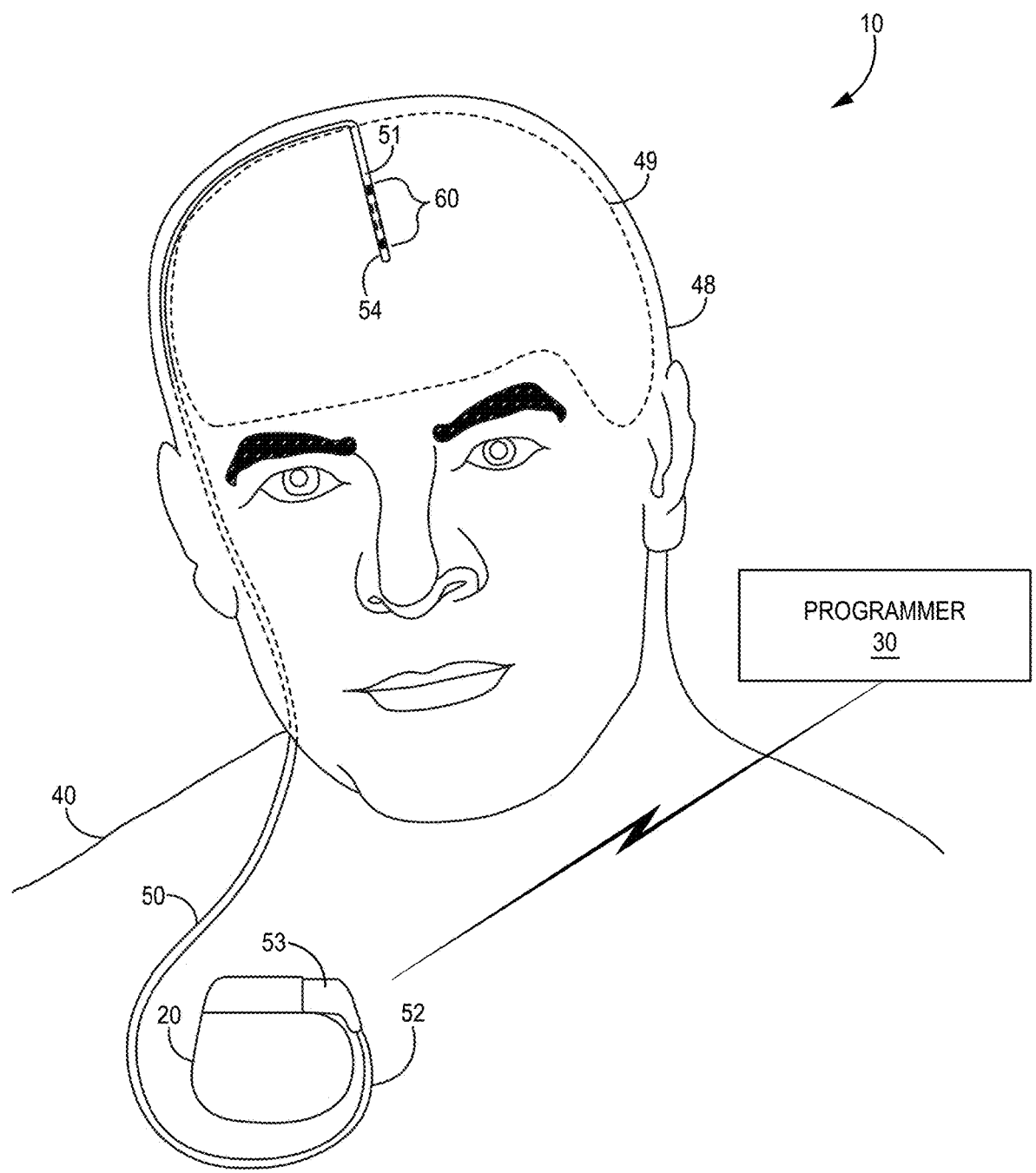
FIG. 1 is a conceptual diagram illustrating a schematic view of an example of a therapy system that delivers electrical stimulation therapy to or receives electrical signals from a patient.

As described above, some examples of the disclosure relate to implantable medical leads, lead extensions, and lead adapters (also referred to as "lead systems," "medical leads," or "leads") that include one or more electrically conductive electrodes and/or one or more electrically conductive terminal connectors (also referred to as "connectors"). Using the lead and electrode, a medical device may deliver or sense electrical signals to provide therapy to a patient to treat a patient condition. Medical leads may include an electrode electrically connected to one or more electrically conductive lead wires (also referred to as "conductors") or other conductive material extending through the lead body to electrically connect to a connector. Electrical stimulation from a medical device electrically connected to the connector may be conducted along the conductors to be delivered across a surface of the electrode.

Certain critical portions of leads, such as portions near electrodes or connectors, may include insulative reinforcing material (also referred to as an "insulator" or "insulative material"), such as epoxy or polymer, around the conductors. This insulative material may provide structural integrity to these critical portions of the leads, reduce movement of the conductors within the lead body by fixing the conductors to the lead body, and/or provide a greater amount of insulation between conductors. However, this rigid insulative material may reduce flexibility of the lead at the critical portions. When the lead is subjected to a bend at these critical portions, especially in configurations in which the conductors are straight and off-axis, the conductors within the lead body may experience high compressive or tensile stresses. If the conductors are not free to relieve these stresses, the conductors may wholly or partially fracture, and the electrical stimulation or other electrical signals may no longer be carried through the fractured conductor.

According to embodiments of the disclosure, a medical lead may include one or more portions of a conductor that are not fixed to a lead body of the lead, but are instead free to move within the lead body to relieve compressive or tensile stresses caused by bends or other movement of the lead, as will be further explained below. For example, a lead may include a conductor and an insulative material surrounding the conductor. However, rather than directly coupling the insulative material to the conductor, the insulative material is coupled to a sleeve that surrounds and directly contacts the conductor to form a conductor assembly. At an unfixed portion of this conductor assembly, the sleeve may not be fixed to the conductor, such that the conductor is free to move within the sleeve relative to the lead body. However, at a fixed portion of this conductor assembly, the sleeve may be fixed to (e.g., forms a mechanical or chemical bond or seal with) the conductor, such that insulative material injected into the lead body during lead manufacture may not flow into the sleeve and restrict movement of the conductor within the unfixed portion of the conductor assembly.

In this way, example leads discussed herein may allow conductors within the leads to self-relieve stress in response to bending or some other stress. For example, in response to a bend about the longitudinal axis of the lead (e.g., from a straight initial position) in the fixed portion of the lead, the conductor may move within the sleeve relative to the surrounding lead body, such as toward the bend in response to tensile stresses or away from the bend in response to compressive stresses. This movement may relieve the compressive and/or tensile stresses created by the bend, thereby reducing the likelihood of the conductor fracturing from those stresses. As such, example leads discussed herein may be positioned in configurations that would ordinarily create significant stresses on conductors within the lead, such as tight bends, such that leads may be placed in more compact and/or varied positions.

Implantable medical leads as discussed herein may be used in a variety of systems, including therapy systems. FIG. 1 is a conceptual diagram illustrating an exemplary therapy system 10 including lead extension 50 and lead 51 implanted in the brain 49 of patient 40. For ease of illustration, examples of the disclosure will primarily be described with regard to implantable electrical stimulation leads and implantable medical devices that apply neurostimulation therapy to brain 49 of patient 40 in the form of deep brain stimulation (DBS). However, the features and techniques described herein may be useful in other types of medical device systems which employ medical leads to deliver electrical stimulation to a patient and/or sense electrical signals via one or more electrodes of the lead. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As shown in FIG. 1, therapy system 10 includes medical device programmer 30, implantable medical device (IMD) 20, lead extension 50, and lead 51. Lead 51 includes plurality of electrodes 60 adjacent a distal end 54 of lead 51. IMD 20 includes switching circuitry that includes an electrical stimulation generator that generates and delivers electrical stimulation therapy to one or more regions of brain 49 of patient 40 via one or more of electrodes 60. In the example shown in FIG. 1, therapy system 10 may be referred to as a DBS system because IMD 20 provides electrical stimulation therapy directly to tissue within brain 49, e.g., a tissue site under the dura mater of brain 49. In other examples, lead 51 may be positioned to deliver therapy to a surface of brain 49 (e.g., the cortical surface of brain 49).

In accordance with examples of the disclosure, lead 51 includes distal end 54 and lead extension 50 includes a proximal end 52 of a lead system that includes lead 51 and lead extension 50. As lead 51 is assembled, respective electrical connection sleeves (not shown in FIG. 1) adjacent proximal end 52 provide an electrical connection between IMD 20 and the conductive pathways of lead 51 running to electrodes 60 adjacent distal end 54 defined by the plurality of conductors of lead extension 50. Using the conductive pathways, IMD 20 may deliver electrical stimulation to patient 40 and/or sense electric signals of patient 40 using lead 51 and lead extension 50.

In the example shown in FIG. 1, IMD 20 may be implanted within a subcutaneous pocket below the clavicle of patient 40. In other examples, IMD 20 may be implanted within other regions of patient 40, such as a subcutaneous pocket in the abdomen or buttocks of patient 40 or proximate the cranium 48 of patient 40. Proximal end 52 of lead extension 50 is coupled to IMD 20 via a connection sleeve block 53 (also referred to as a header 53), which may include, for example, electrical contacts that electrically couple to respective electrical contacts at proximal end 52 of lead extension 50. The electrical contacts electrically couple the electrodes 60 carried by distal end 54 of lead 51 to IMD 20 through conductors (not shown). Lead extension 50 and lead 51 traverse from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as processing circuitry, therapy circuitry, and memory.

To secure these conductors in place and provide extra insulation between electrical contacts at critical portions of lead extension 50 and/or lead 51, such as proximal end 52 and distal end 54, respectively, one or more critical portions of lead extension 50 and/or lead 51 may be filled with a rigidizing reinforcing insulative material, such as an epoxy or polymer. Critical portions may include, for example, portions of lead extension 50 that are intended for contact with IMD 20. However, in this example, this insulative material may reduce flexibility of lead extension 50 at the critical portions, such that bends in lead extension 50 at these critical portions may have high compressive and/or tensile stresses. These stresses may lead to breakage of conductors within lead extension 50. For example, as shown in FIG. 1, lead extension 50 may have a bend near proximal end 52 where lead extension 50 couples to IMD 20. This bend may enable lead extension 50 to be positioned and routed near IMD 20, such that lead extension 50 may be less invasive than if lead extension 50 was positioned away from IMD 20. However, this bend may be at a critical portion such that, without a stress-relieving mechanism, conductors near the bend may be susceptible to breaking. According to embodiments of the disclosure, lead extension 50 may include stress-relieving portions in which the conductors of lead extension 50 near an end of lead extension 50 are not fixed to a body of lead extension 50, but are instead free to move, thereby relieving compressive or tensive stresses caused by bends or other movement of lead extension 50, as will be further explained below.

Lead 51 may be positioned to deliver electrical stimulation to one or more target tissue sites within brain 49 to manage patient symptoms associated with a disorder of patient 40. Lead 51 may be implanted to position electrodes 60 at desired locations of brain 49 through respective holes in cranium 48. Lead 51 may be placed at any location within brain 49 such that electrodes 60 are capable of providing electrical stimulation to target tissue sites within brain 49 during treatment. Although FIG. 1 illustrates system 10 as including a single lead 51 coupled to IMD 20, in some examples, system 10 may include more than one lead.

Lead 51 may deliver electrical stimulation via electrodes 60 to treat any number of neurological disorders or diseases in addition to movement disorders, such as seizure disorders or psychiatric disorders. Lead 51 may be implanted within a desired location of brain 49 via any suitable technique, such as through respective burr holes in a skull of patient 40 or through a common burr hole in the cranium 48. Lead 51 may be placed at any location within brain 49 such that electrodes 60 of lead 51 are capable of providing electrical stimulation to targeted tissue during treatment. In the examples shown in FIG. 1, electrodes 60 of lead 51 are shown as segmented electrodes and ring electrodes. Electrodes 60 of lead 51 may have a complex electrode array geometry that is capable of producing shaped electrical fields. In this manner, electrical stimulation may be directed to a specific direction from lead 51 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, therapy system 10 monitors electrical signals, such as, e.g., one or more bioelectrical brain signals of patient 40. For example, IMD 20 may include sensing circuitry that senses bioelectrical brain signals within one or more regions of brain 49. In the example shown in FIG. 1, the signals generated by electrodes 60 are conducted to the sensing circuitry within IMD 20 via conductors within lead 51 and lead extension 50, including one or more conductors within lead 51 and lead extension 50 between distal end 54 of lead 51 and proximal end 52 of lead extension 50.

Programmer 30 wirelessly communicates with IMD 20 as needed to provide or retrieve therapy information. Programmer 30 is an external computing device that the user, e.g., the clinician and/or patient 40, may use to communicate with IMD 20. For example, programmer 30 may be a clinician programmer that the clinician uses to communicate with IMD 20 and program one or more therapy programs for IMD 20. Alternatively, programmer 30 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 30 may be a hand-held computing device with a display viewable by the user and an interface for providing input to programmer 30 (i.e., a user input mechanism). In other examples, programmer 30 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 30.

Again, while lead 51 is described here for use in DBS applications, lead 51 or other leads may be implanted at any other location within patient 40. For example, lead 51 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

Figure 2:
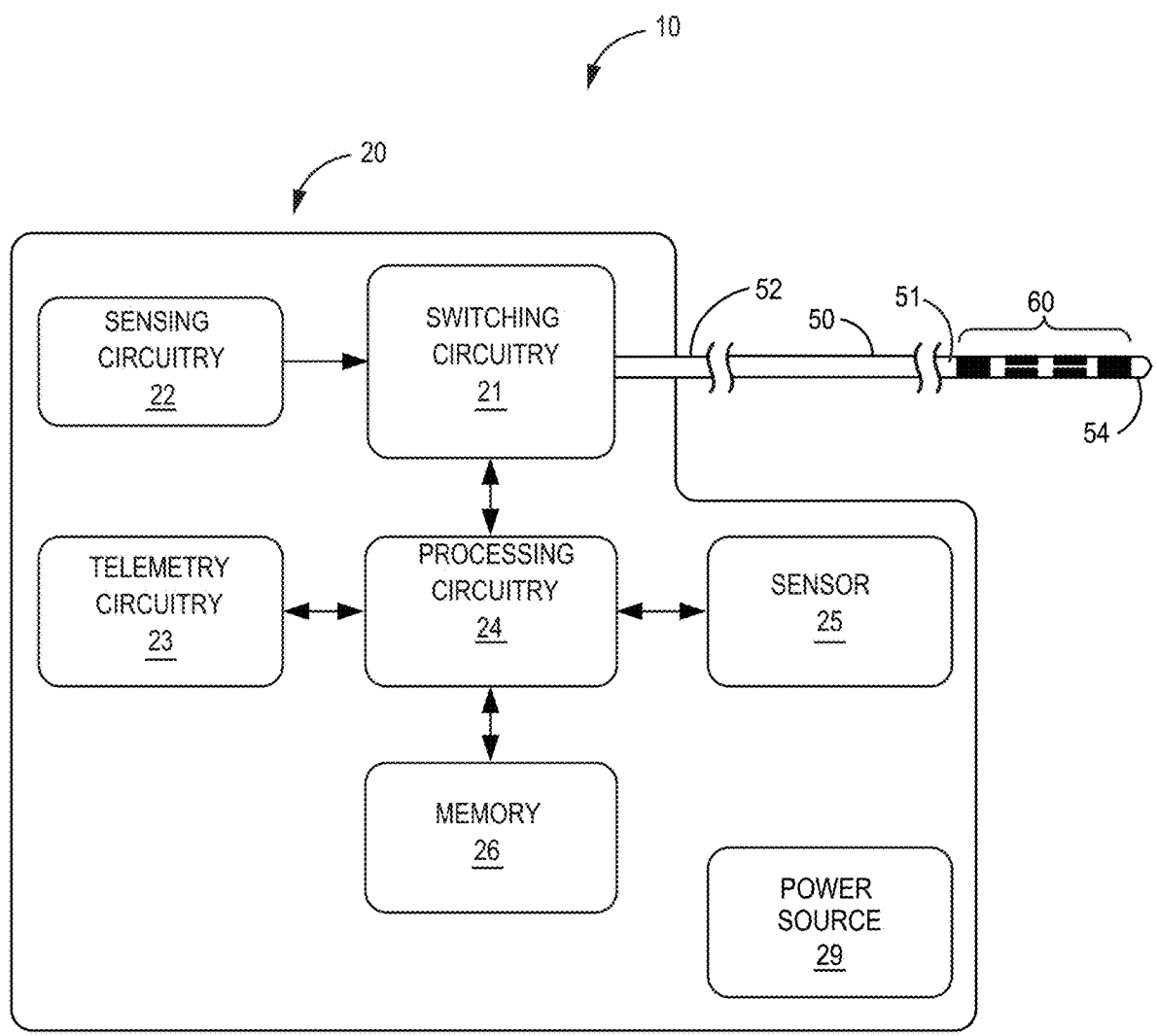
FIG. 2 is a conceptual block diagram of a schematic view of an example of a medical device system.

FIG. 2 is a functional block diagram illustrating components of IMD 20. As shown, therapy system 10 includes IMD 20 coupled to lead 51 through lead extension 50. In the example of FIG. 2, IMD 20 includes processing circuitry 24, memory 26, switching circuitry 21, sensing circuitry 22, telemetry circuitry 23, sensor 25, and power source 29. Processing circuitry 24 may include any one or more microprocessors, controllers, digital signal processors (DSPs), application specific integrated circuits (ASICs), field-programmable gate arrays (FPGAs), or discrete logic circuitry. The functions attributed to processors described herein, including processing circuitry 24, may be provided by processing circuitry of a hardware device, e.g., as supported by software and/or firmware. Processing circuitry 24 controls switch circuitry to apply particular stimulation parameter values, such as amplitude, pulse width, and pulse rate.

Memory 26 may include any volatile or non-volatile media, such as a random-access memory (RAM), read only memory (ROM), non-volatile RAM (NVRAM), electrically erasable programmable ROM (EEPROM), flash memory, and the like. Memory 26 may store computer-readable instructions that, when executed by processing circuitry 24, cause IMD 20 to perform various functions. Memory 26 may be a storage device or other non-transitory medium.

In the example shown in FIG. 2, lead 51 includes electrodes 60 located at distal end 54. Processing circuitry 24 also controls switching circuitry 21 to generate and apply the stimulation signals, which may be generated by a stimulation generator, to selected combinations of electrodes. In some examples, switching circuitry 21 couples stimulation signals to selected conductors within lead 51 and lead extension 50, which, in turn, delivers the stimulation signals across selected electrodes. Such switching circuitry 21 may be a switch array, switch matrix, multiplexer, or any other type of switching circuitry configured to selectively couple stimulation energy to selected electrodes and to selectively sense bioelectrical neural signals of the spine with selected electrodes.

In other examples, however, a stimulation generator does not include switching circuitry. In these examples, the stimulation generator comprises a plurality of pairs of voltage sources, current sources, voltage sinks, or current sinks connected to each of electrodes such that each pair of electrodes has a unique signal generator. In other words, in these examples, each of electrodes is independently controlled via its own signal generator (e.g., via a combination of a regulated voltage source and sink or regulated current source and sink), as opposed to switching signals between electrodes.

Switching circuitry 21 may be a single channel or multi-channel stimulation generator. In particular, switching circuitry 21 may be capable of delivering a single stimulation pulse or multiple stimulation pulses at a given time via a single electrode combination or multiple stimulation pulses at a given time via multiple electrode combinations. In some examples, however, switching circuitry 21 may be configured to deliver multiple channels on a time-interleaved basis. For example, switching circuitry 21 may serve to time divide the output of switching circuitry 21 across different electrode combinations at different times to deliver multiple programs or channels of stimulation energy to patient 40. In another example, switching circuitry 21 may control the independent sources or sinks on a time-interleaved bases.

Lead extension 50 may include distal end 54 including a complex electrode array geometry, but may also include one or more single ring electrodes along the longitudinal axis in other examples. In one example, distal end 54 of lead 51 includes a plurality of electrodes 60 positioned at different axial positions along the longitudinal axis of the lead and a plurality of electrodes 60 positioned at different angular positions around the circumference of the lead (which may be referred to as electrode segments). In this manner, electrodes may be selected along the longitudinal axis of lead 51 and along the circumference of the lead. Selectively activating electrodes 60 of lead 51 can produce customizable stimulation fields that may be directed to a particular side of lead 51 in order to isolate the stimulation field around the target anatomical region of brain 49. These techniques may also be applied to leads having more or fewer than two ring electrodes. In yet other cases, lead 51 may include only segmented electrodes or only ring electrodes.

Although sensing circuitry 22 is incorporated into a common housing with switching circuitry 21 and processing circuitry 24 in FIG. 2, in other examples, sensing circuitry 22 may be in a separate housing from IMD 20 and may communicate with processing circuitry 24 via wired or wireless communication techniques. Example bioelectrical signals include, but are not limited to, a signal generated from local field potentials within one or more regions of the spine or brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead extension 50 or other leads. In addition, IMD 20 may receive sensor signals wirelessly from remote sensors via telemetry circuitry 23, for example. In some examples, one or more of these remote sensors may be external to patient (e.g., carried on the external surface of the skin, attached to clothing, or otherwise positioned external to the patient).

Telemetry circuitry 23 supports wireless communication between IMD 20 and an external programmer (e.g., such as programmer 30) or another computing device under the control of processing circuitry 24. Processing circuitry 24 of IMD 20 may receive, as updates to programs, values for various stimulation parameters such as amplitude and electrode combination, from programmer 30 via telemetry circuitry 23. Telemetry circuitry 23 in IMD 20, as well as telemetry circuitry in other devices and systems described herein, such as programmer 30, may accomplish communication by radiofrequency (RF) communication techniques. In addition, telemetry circuitry 23 may communicate with external medical device programmer 30 via proximal inductive interaction of IMD 20 with programmer 30. Accordingly, telemetry circuitry 23 may send information to programmer 30 on a continuous basis, at periodic intervals, or upon request from IMD 20 or programmer 30.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

Figure 3A:
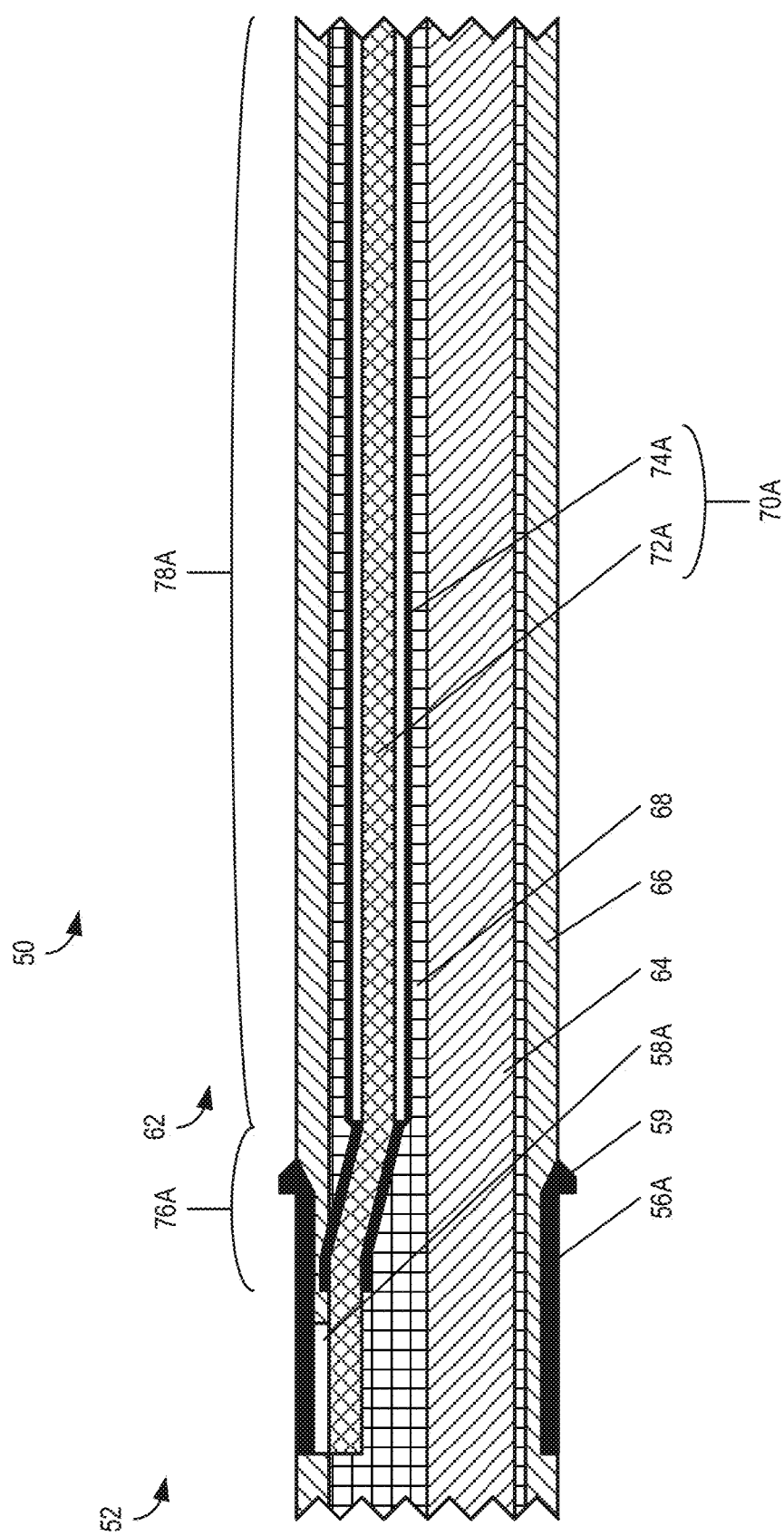
FIG. 3A is a conceptual diagram illustrating a longitudinal cross-sectional view of an example medical lead.

As explained above, implantable medical leads discussed herein may include conductors capable of relieving stress by moving relative to a surrounding lead body. FIG. 3A is a conceptual diagram illustrating a longitudinal cross-sectional view of proximal end 52 of example medical lead extension 50 that includes stress-relieving mechanisms discussed herein. Such areas proximate to proximal end 52 near a connection with IMD 20 may have tight bends that exert considerable tensile and/or compressive stresses on conductors within lead extension 50. While these stress-relieving mechanisms will be described with respect to proximal end 52 for a single conductor assembly 70A, it will be understood that these principles apply to other portions of lead extension 50 and/or for a plurality of conductor assemblies and their corresponding conductors and sleeves. Further, it will be understood that other implantable medical devices may utilize the techniques discussed herein to relieve stresses on conductors within the implantable medical devices.

Lead extension 50 includes a lead body 62 extending between a distal end (e.g. distal end 54 of FIG. 1) and proximal end 52 that define a longitudinal axis of lead body 62. Lead body 62 may be configured to provide structure to lead extension 50 and/or encase various functional components, such as conductors and connectors, of lead extension 50. At proximal end 52 shown in FIG. 3A, lead body 62 includes a lumen 64, a jacket 66, and an insulative material 68. Jacket 66 may be configured to encase components of lead extension 50 and form an outer surface of lead extension 50. A variety of materials may be used for jacket 66 including, but not limited to, polyurethane (e.g., 55D, 80A, 75D, etc.), silicone, silicon-polyurethane blends, and the like. Lumen 64 may be configured to receive a stylet, guidewire, or other guiding device for positioning lead extension 50 within a patient. For example, lumen 64 may include one or more structures that engage with the guiding device. In the example of FIG. 3A, lumen 64 is shown off-axis, such that one or more conductors may be positioned around the longitudinal axis opposite lumen 64; however, in some examples, lumen 64 may be a central lumen, such that the longitudinal axis extends through lumen 64 and a plurality of conductors may be positioned around lumen 64.

Insulative material 68 may be configured to provide structure to lead extension 50 within jacket 66. For example, insulative material 68 may include a rigid material capable of securing one or more conductors in place within lead extension 50 and maintaining a structural integrity of lead extension 50 at portions of lead extension 50 that include insulative material 68. Insulative material 68 may be formed from a polymeric material including, but not limited to, polyurethanes, silicones, fluoropolymers, fluoroelastomers, polyethylenes, polyesters, epoxies, and other biocompatible polymers suitable for contact with bodily tissue. In some examples, insulative material 68 includes more than one material. For example, insulative material 68 may include a first material, such as an elastic polymer, that contacts an inner surface of jacket 66 and includes channels for conductor assemblies, as will be discussed further below. Insulative material 68 may further include a second material, such as a rigid polymer, that contacts an outer surface of the conductor assemblies within the channels of the first material.

While lead body 62 includes insulative material 68 at proximal end 52, at other portions of lead extension 50, lead body 62 may contain greater or fewer components, such as no insulative material 68. For example, it may be desired that other portions of lead extension 50 further away from proximal end 52 be free of insulative material, as rigidity may not provide as great of a structural advantage at such portions.

While not shown, lead extension 50 may include one or more securing mechanisms configured to engage with a medical device, such as a connection header 53 of IMD 20 of FIG. 1, to secure lead extension 50 to the device and/or limit a distance of insertion of lead extension 50 into the device. For example, proximal end 52 of lead extension 50 forms a male connector that is inserted into a female connector like a plug. Within header 53 may be electrical contacts that align with the electrical connectors 56 on proximal end 52 of lead extension 50. Ridge 59 on connector 56A may prevent lead extension 50 from extending beyond a set distance into header 53. While a ridge is shown in FIG. 3A, a variety of securing mechanisms may be used including, but not limited to, clips, magnets, screws, and the like.

Proximal end 52 of lead extension 50 includes one or more connectors. While only a single electrical connector 56A is shown, lead extension 50 may include multiple connectors, each connector electrically connected to at least one conductor, such as will be described in FIG. 3B. Electrical connector 56A may be electrically coupled to conductor 72A within lead body 62 and may be configured to electrically couple to a conductive contact external of lead extension 50, such as a contact of IMD 20 of FIG. 1 or 2. Electrical connector 56A may be positioned at or near proximal end 52 of lead extension 50, such that IMD 20 may receive proximal end 52 and electrically coupled to electrical connector 56A. In some examples, electrical connector 56A may be a ring contact that extends around an outer perimeter of lead extension 50. Electrical connector 56A may be formed from an electrically conductive material including, but not limited to, platinum, palladium, iridium, titanium and titanium alloys such as titanium molybdenum alloy (TiMoly), nickel and nickel alloys such as MP35N alloy, and the like.

Figure 3B:
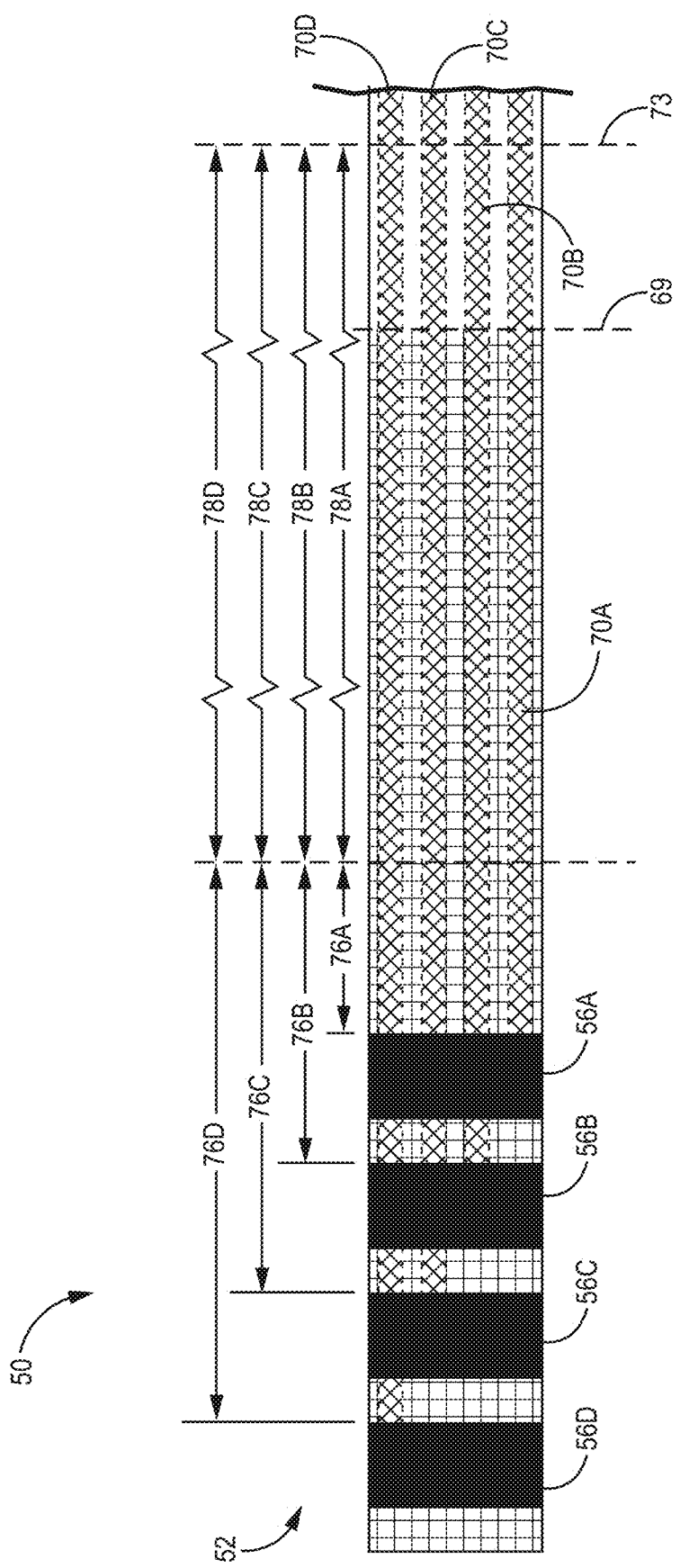
FIG. 3B is a conceptual diagram illustrating a partial cut-away, top view of an example medical lead with a pass-through view of conductor assemblies.

In example designs of medical leads, a conductor may be directly fixed to a polymer fill, such as insulative material 68, of a lead. In these example designs, the conductor may not move relative to the polymer fill, such that stresses exerted on the polymer fill may be transferred to the conductor. In contrast to these example designs, lead extension 50 includes one or more conductor assemblies, such as conductor assembly 70A, within lead extension 50 that are configured to allow relative movement of conductors, such as conductor 72A, within the respective conductor assemblies. In the example of FIG. 3A, only one conductor assembly 70A is shown; however, as illustrated in FIG. 3B, lead extension 50 may include a plurality of conductor assemblies, such that lead extension 50 includes a plurality of conductors and a plurality of connectors. As such, descriptions and configurations of conductor assembly 70A, conductor 72A, a sleeve 74A, and electrical connector 56A may apply to other conductors within and connectors on lead extension 50.

Conductor assembly 70A includes electrical conductor 72A. Electrical conductor 72A extends about the longitudinal axis of lead body 62. Electrical conductor 72A is electrically coupled to electrical connector 56A, such as through connector sleeve 58A, and a conductive element at a distal end of lead extension 50, such as an electrode, a set screw, or another conductive element. A variety of methods may be used to electrically couple electrical connector 56A to electrical conductor 72A including, but not limited to, laser welding, crimping, resistance welding, swaging, and the like. Conductor 72A may be electrically isolated from other conductors by lead body 62 to form separate channels, circuits, or conductive paths through the lead body 62. In some examples, conductor 72A may include an electrical insulator sheath around a conductive portion. The electrical insulator sheath may be configured to electrically insulate conductor 72A from undesired contact with another component within lead extension 50, such as an electrode or connector for which electrical contact is not intended for conductor 72A. In some examples, conductor 72A may include a coating, such as a low friction coating. In some examples, conductor 72A may have a diameter, with or without the electrical insulator sheath, between at least about 0.0025 in. and about 0.0080 in. Conductor 72A may have a distal connection portion on a distal end and a proximal connection portion on a proximal end. The distal and proximal connection portions may be configured to electrically couple conductor 72A to electrical connector 56A and an electrode, such as one of electrodes 60 shown in FIGS. 1 and 2. In some examples, conductor 72A may include two or more strands of conductive material that are braided or cabled. In some examples, conductor 72A may include one or more filars that are coiled.

Conductor assembly 70A includes a sleeve 74A positioned around conductor 72A. An outer surface of sleeve 74A is coupled to (i.e., in contact with or attached to) insulative material 68 of lead body 62, such that sleeve 74A may be fixed to lead body 62. An inner surface of sleeve 74A contacts conductor 72A. In some examples, sleeve 74A has a thickness less than about 1 mm. In some examples, sleeve 74A may have a thickness between about 0.0005 inches (about 13 µm) and about 0.010 inches (about 0.25 mm).

Sleeve 74A is configured to allow one or more portions of conductor 72A to move within sleeve 74A in response to compressive or tensile forces on conductor 72A experienced during ordinary operating conditions for lead extension 50. Sleeve 74A includes a fixed portion 76A that is fixed to electrical conductor 72A. For example, fixed portion 76A may be chemically or mechanically coupled to conductor 72A such that conductor 72A and sleeve 74A may prevent insulative material 68 from entering into sleeve 74A. In some examples, fixed portion 76A may be fixed such that an end of sleeve 74A is sealed from liquids penetrating between an outer surface of conductor 72A and an inner surface of sleeve 74A.

In some examples, conductor 72A may not move within a fixed portion 76A under normal operating conditions of lead extension 50. In some examples, fixed portion 76A may be fixed to electrical conductor 72A, such that electrical conductor 72A may not be configured to axially move within sleeve 74A in response to a flex of lead body 62. For example, in response to a flex of lead body 62 of a relatively sharp angle, such as about 90 degrees, at a relatively sharp radius, such as a radius of about five centimeters, electrical conductor 72A may axially move not within and relative to sleeve 74A (e.g., during a flex test of both fixed portion 76A and unfixed portion 78A, such as illustrated in Test Method 3 below). In some examples, fixed portion 76A may be fixed to electrical conductor 72A such that electrical conductor 72A may have an adhesion with fixed portion 76A that is sufficiently high to prevent electrical conductor 72A from axially moving within fixed portion 76A in response to tension or compression on electrical conductor 72A. For example, electrical conductor 72A may have an adhesion with fixed portion 76A that corresponds to a mean maximum removal load of electrical conductor 72A of greater than about 1 Newton per meter of sleeve 74A (e.g., if electrical conductor 72A undergoes a cable removal test or other tensile load test with only sleeve 74A, such as illustrated in Test Method 1 below).

Sleeve 74A also includes an unfixed portion 78A that is not fixed to electrical conductor 72A. For example, unfixed portion 78A may not be chemically or mechanically coupled to conductor 72A (or may be chemically or mechanically coupled to a low degree), such that conductor 72A may move within unfixed portion 78A under normal operating conditions of lead extension 50. In some examples, electrical conductor 72A may be unfixed to unfixed portion 78A, such that electrical conductor 72A may be configured to axially move within unfixed portion 78A in response to a flex of lead body 62. For example, in response to a flex of lead body 62 of a relatively sharp angle, such as about 90 degrees, at a relatively sharp radius, such as a radius of about five centimeters, electrical conductor 72A may axially move within and relative to unfixed portion 78A, such that stress created by the flex may be relieved (e.g., during a flex test of both fixed portion 76A and unfixed portion 78A, as illustrated in Test Method 1 below). In some examples, electrical conductor 72A may be unfixed to sleeve 74A such that electrical conductor 72A may have an adhesion with unfixed portion 78A that is sufficiently low to permit electrical conductor 72A to axially move within unfixed portion 78A in response to tension or compression on electrical conductor 72A. For example, electrical conductor 72A may have an adhesion with unfixed portion 78A that corresponds to a mean maximum removal load of electrical conductor 72A of less than about 0.1 Newtons per meter of sleeve 74A (e.g., if electrical conductor 72A undergoes a cable removal test or other tensile load test with only unfixed portion 78A of sleeve 74A, as illustrated in Test Method 1 below). In this way, insulative material 68 may still provide structural support to particular portions of lead extension 50, such as proximal end 52, without mechanically locking conductors into position for a length of insulative material 68, thus allowing conductors 72 to self-relieve stress.

Figure 3C:
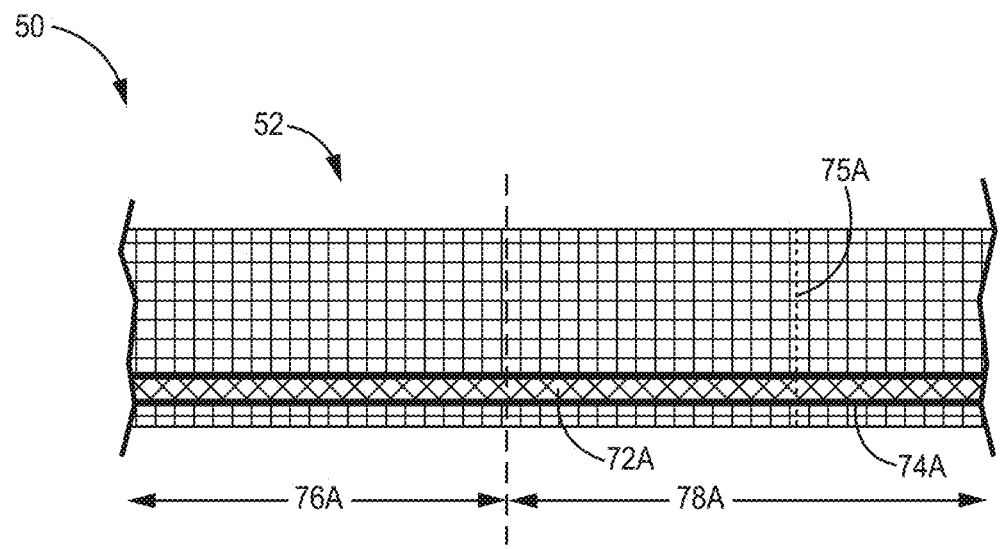
FIG. 3C is a longitudinal cross-sectional diagram illustrating a section of a proximal end of a lead extension in a straightened configuration.
Figure 3D:
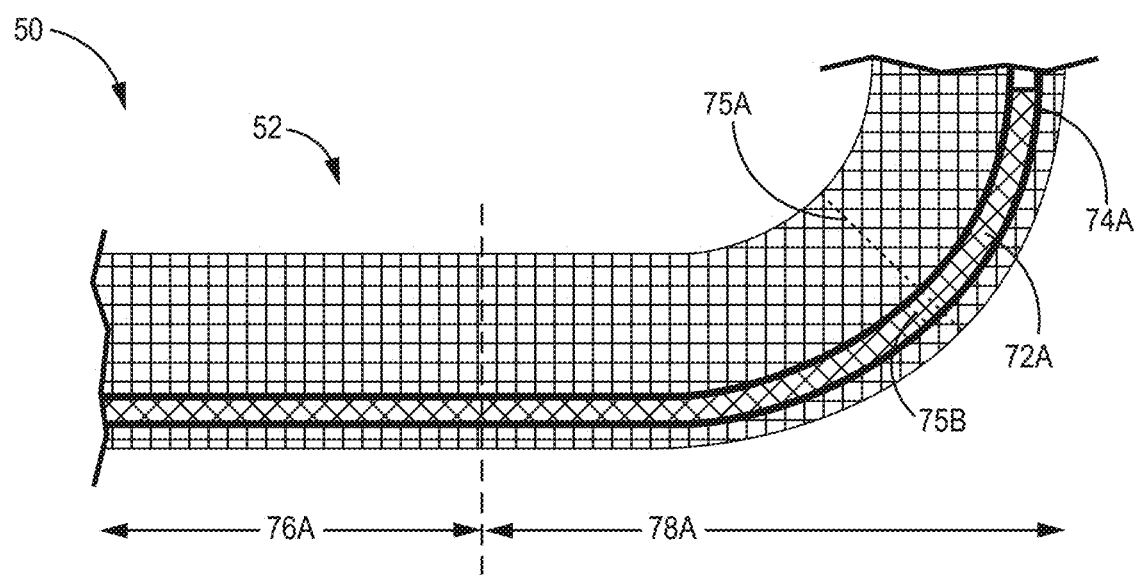
FIG. 3D is a longitudinal cross-sectional diagram illustrating a section of a proximal end of a lead extension in a bent configuration.

FIGS. 3C and 3D are simplified longitudinal cross-sectional diagrams illustrating a section of proximal end 52 of lead extension 50 that includes conductor 72A in sleeve 74A. Sleeve 74A includes fixed portion 76A and unfixed portion 78A. FIG. 3C illustrates lead extension 50 in a straightened configuration, such that conductor 72A within sleeve 74A is in a first position indicated by line 75A. FIG. 3D illustrates lead extension 50 in a bent configuration, such that conductor 72A within sleeve 74A moves within sleeve 74A to a second position indicated by line 75B, which has moved relative to first position indicated by line 75A. As such, in unfixed portion 78A of sleeve 74A, conductor 72A moves relative to sleeve 74A, and thus the lead body. However, if the bend was in fixed portion 76A of sleeve 74A, rather than unfixed portion 78A of sleeve 74A, conductor 72A would not move relative to sleeve 74A.

Referring back to FIG. 3A, in some examples, fixed portion 76A may be configured to seal a proximal end of sleeve 74A against conductor 72A. For example, fixed portion 76A may be positioned at a proximal end of sleeve 74A and/or proximal end 52 of lead extension 50, such as near electrical connector 56A. As will be explained in step 136 of FIG. 6 below, such a position of fixed portion 76A may seal a proximal end of sleeve 74A and enable conductor assembly 70A to be surrounded by insulative material 68 without material intended for insulative material 68 flowing into sleeve 74A and inadvertently fixing conductor 72A to sleeve 74A or insulative material 68. However, a corresponding distal end of sleeve 74A may not be fixed to conductor 72A, as insulative material 68 may not extend to the distal end of sleeve 74A. In some examples, fixed portion 76A may be positioned within about 2 inches (about 5 cm) from proximal end 52 of lead extension 50, such as proximate to electrical connector 56A. In some examples, fixed portion 76A of sleeve 74A is proximal to unfixed portion 78A of sleeve 74A. For example, fixed portion 76A may be at a proximal end of sleeve 74A, such that a remainder of sleeve 74A may be unfixed portion 78A.

Fixed portion 76A may have a variety of lengths, such that fixed portion 76A may secure conductor 72A into sleeve 74A at fixed portion 76A. The length of fixed portion 76A may be selected according to a variety of factors including, but not limited to, a distance to ensure sealing of conductor assembly 70A from insulative material 68 during manufacture (e.g., dependent on viscosity or surface tension of insulative material 68 during injection), space constraints within lead extension 50, a number of connectors 56, a spacing of connectors 56, an anticipated bending location of lead extension 50, a removal load of fixed portion 76A, and the like. In some examples, the length of fixed portion 76A at proximal end 52 may be between about 0.05 inches (about 0.13 cm) and about 1 inch (about 2.5 cm) beyond a distalmost electrical connector at proximal end 52. While fixed portion 76A has been described with respect to a single portion of sleeve 74A, in some examples, conductor assembly 70A may include a plurality of fixed portions. For example, a distal end of lead 51 may include a fixed portion proximate to a plurality of electrodes and an unfixed portion proximal to the fixed portion.

In some examples, such as proximal end 52 of lead extension 50, unfixed portion 78A may be positioned distal to fixed portion 76A. For example, once a proximal end of sleeve 74A is sealed, a remainder of sleeve 74A may be part of unfixed portion 78A. Unfixed portion 78A may be configured to allow conductor 72A to move relative to sleeve 74A in areas of high stress, such as portions of lead extension 50 proximate to proximal end 52. Such portions may of lead extension 50 may be routed at relatively sharp angles from IMD 20. In some examples, a proximal end of unfixed portion 78A of sleeve 74A is less than about 10 cm from a distal-most electrical connector, while a distal end of unfixed portion 78A may extend up to a distal end of lead extension 50. Unfixed portion 78A may have a variety of lengths. In some examples, unfixed portion 78A of sleeve 74A has a length greater than about 2.5 cm, such as greater than a proximal end of a portion of lead body 62 filled with insulative material 68. For example, as discussed above, fixed portion 76A may prevent insulative material 68 from flowing into a proximal end of sleeve 74A. To prevent insulative material 68 from flowing into a distal portion of sleeve 74A, a length of sleeve 74A may be selected such that the distal end of sleeve 74A extends beyond an anticipated fill line of insulative material 68, as will be described in FIG. 3B below.

To form fixed portion 76A and unfixed portion 78A, sleeve 74A may be configured to be selectively fixed to fixed portion 76A while remaining unfixed to unfixed portion 78A. Sleeve 74A may be configured to be fixed to conductor 72A using a variety of mechanisms. In some examples, sleeve 74A is configured to radially shrink in response to a stimulus, such that a diameter of an inner surface of sleeve 74A is reduced to exert a force on conductor 72A sufficient to fix sleeve 74A against conductor 72A and/or seal sleeve 74A against conductor 72A. Mechanisms for fixing sleeve 74A to conductor 72A may include, but are not limited to, thermal-shrink, chemical shrink, adhesion, and the like. In some examples, sleeve 74A is a thermal-shrink sleeve, such that a length of sleeve 74A exposed to a heat source may shrink to form fixed portion 76A. A variety of thermal-shrink materials may be used for sleeve 74A including, but not limited to, polyolefin, polypropylene, and the like. In some examples, sleeve 74A is a tube, such that sleeve 74A entirely surrounds conductor 72A at a circumference.

FIG. 3B is a conceptual diagram illustrating a partial cut-away, top view of an example lead extension 50 that includes four ring electrical connectors 56A, 56B, 56C, and 56D (collectively referred to as "connectors 56"). Each of connectors 56 is electrically coupled to a respective conductor of conductor assembly 70A, 70B, 70C, and 70D (collectively referred to as "conductor assemblies 70"). Each conductor assembly 70A, 70B, 70C, and 70D includes a sleeve having a respective fixed portion 76A, 76B, 76C, and 76D (collectively referred to as "fixed portions 76") that is fixed to a conductor and a respective unfixed portion 78A, 78B, 78C, and 78D (collectively referred to as "unfixed portions 78") that is not fixed to the conductor. While fixed portions 76 are shown as having different lengths and unfixed portions 78 are shown as having a same length, each of fixed portions 76 and each of unfixed portions 78 may have same or different lengths. For example, insulative material 68 may extend to a particular fill line 69 of lead extension 50 from proximal end 52 that is less than a length 73 of a respective sleeve of conductor assemblies 70, such that portions of conductors 72 within unfixed portions 78 of sleeves 74 are free to move and portions of conductors 72 beyond fill line 69 of insulative material 68 are free to move.

In some examples, sleeve 74A may be substantially sealed from liquids penetrating between an outer surface of conductor 72A and an inner surface of sleeve 74A by maintaining a low clearance between the outer surface of conductor 72A and the inner surface of sleeve 74A. FIG. 3E is a conceptual diagram illustrating a longitudinal cross-sectional view of proximal end 52 of example medical lead extension 50 that includes stress-relieving mechanisms discussed herein.

In the example of FIG. 3E, conductor assembly 70A includes a fixed portion 77 in which electrical conductor 72A is fixed to insulative material 68. For example, in fixed portion 77, an insulator of conductor 72A may be chemically and/or mechanically coupled to insulative material 68 to fix conductor 72A within lead extension 50. In some examples, conductor 72A may not move within a fixed portion 77 under normal operating conditions of lead extension 50 when fixed or coupled to insulative material 68.

In the example of FIG. 3E, conductor assembly 70A also includes an unfixed portion 79 that includes sleeve 74A. Sleeve 74A is not directly fixed to electrical conductor within unfixed portion 79, such that conductor 72A is moveable relative to sleeve 74A within sleeve 74A. For example, sleeve 74A may not be chemically or mechanically coupled to conductor 72A (or may be chemically or mechanically coupled to a low degree), such that conductor 72A may axially move within sleeve 74A (i.e., move along a central axis of a lumen of sleeve 74A) under normal operating conditions of lead extension 50. As a result, sleeve 74A is configured to allow substantially all of conductor 72A to move within sleeve 74A in response to compressive or tensile forces on conductor 72A experienced during ordinary operating conditions for lead extension 50.

In some examples, electrical conductor 72A may be unfixed to sleeve 74A, such that electrical conductor 72A may be configured to axially move within sleeve 74A in response to a flex of lead body 62. For example, in response to a flex of lead body 62 of a relatively sharp angle, such as about 90 degrees, at a relatively sharp radius, such as a radius of about five centimeters, electrical conductor 72A may axially move within and relative to sleeve 74A, such that stress created by the flex may be relieved. In some examples, electrical conductor 72A may be unfixed to sleeve 74A such that electrical conductor 72A may have an adhesion with sleeve 74A that is sufficiently low to permit electrical conductor 72A to axially move within sleeve 74A in response to tension or compression on electrical conductor 72A. For example, electrical conductor 72A may have an adhesion with sleeve 74A that corresponds to a mean maximum removal load of electrical conductor 72A of less than about 0.1 Newtons per meter of sleeve 74A (e.g., if electrical conductor 72A undergoes a cable removal test or other tensile load test with only sleeve 74A).

In some examples, fixed portion 77 may be configured to seal a proximal end of sleeve 74A against conductor 72A. For example, sleeve 74A and electrical conductor 72A may have a sufficiently low clearance between each other such that a proximal end 75 of sleeve 74A is sealed from liquids penetrating between an outer surface of conductor 72A and an inner surface of sleeve 74A. Such a low clearance between sleeve 74A and electrical conductor 72A may seal proximal end 75 of sleeve 74A and enable conductor assembly 70A to be surrounded by insulative material 68 without material intended for insulative material 68 flowing into sleeve 74A and inadvertently fixing conductor 72A to sleeve 74A or insulative material 68. In this way, insulative material 68 may still provide structural support to particular portions of lead extension 50, such as proximal end 52, without mechanically locking conductors into position for a length of insulative material 68, thus allowing conductors 72 to self-relieve stress.

Sleeve 74A and electrical conductor 72A may have a variety of clearances, such that conductor 72A and sleeve 74A may prevent insulative material 68 from entering into sleeve 74A. A clearance between conductor 72A and sleeve 74A may be defined by a distance or gap between the outer surface of conductor 72A and inner surface of sleeve 74A. The clearance between sleeve 74A and electrical conductor 72A may be selected according to a viscosity or surface tension of insulative material 68 during injection. For example, prevention of insulative material 68 from entering sleeve 74A may not include, in some examples, an actual seal or bond between the outer surface of conductor 72A and the inner surface of sleeve 74A, but may instead rely on a surface tension or viscosity in combination with the low clearance to prevent insulative material 68 from entering. In some examples, the clearance between sleeve 74A and electrical conductor 72A may be between about 12.5 microns (0.0005 inches) and about 125 microns (0.005 inches). In some instances, such as for a relatively tight fitting but compliant sleeve 74A, sleeve 74A and electrical conductor 72A may have no clearance, as sleeve 74A may cause insufficient compressive force to fix electrical conductor 72A to sleeve 74A under ordinary bending forces experienced on lead extension 50. In some examples, an average molecular weight of insulative material 68 may be greater than about 100,000, such that insulative material 68 may have a relatively high viscosity. A variety of materials may be used for insulative material 68 including, but not limited to, polyurethane, silicone, and the like.

The implantable medical leads discussed herein may include a variety of designs, such as lead extension 50 of FIGS. 1, 2, 3A, 3B, and 3E. FIG. 4A is a conceptual diagram illustrating a side view of proximal end 52 of lead extension 50 without insulative material and a jacket (not shown of ease of illustration), while FIG. 4B is a conceptual diagram illustrating a side view of proximal end 52 of lead extension 50 with insulative material and jacket 66. Proximal end 52 includes a plurality of conductor assemblies 70 and a plurality of electrical connectors 56, such that an electrical conductor of each conductor assembly 70 is coupled to an electrical connector 56. Proximal end 82 includes a reflow band 98 surrounding a plurality of electrical conductors 72 of the plurality of conductor assemblies 70. Proximal end 82 includes a retention sleeve 97.

FIG. 4C is a cross-sectional side view diagram of a section of proximal end 52 of lead extension 50. As illustrated in FIG. 4C, during bending of proximal end 52 as indicated by A, electrical conductor 72 moves inside sleeve 74, as indicated by B. This movement B reduces strain on electrical conductor 72 by pulling electrical conductor 72 into and out of reflow band 98 during tension and compression, as indicated by C.

Figure 4D:
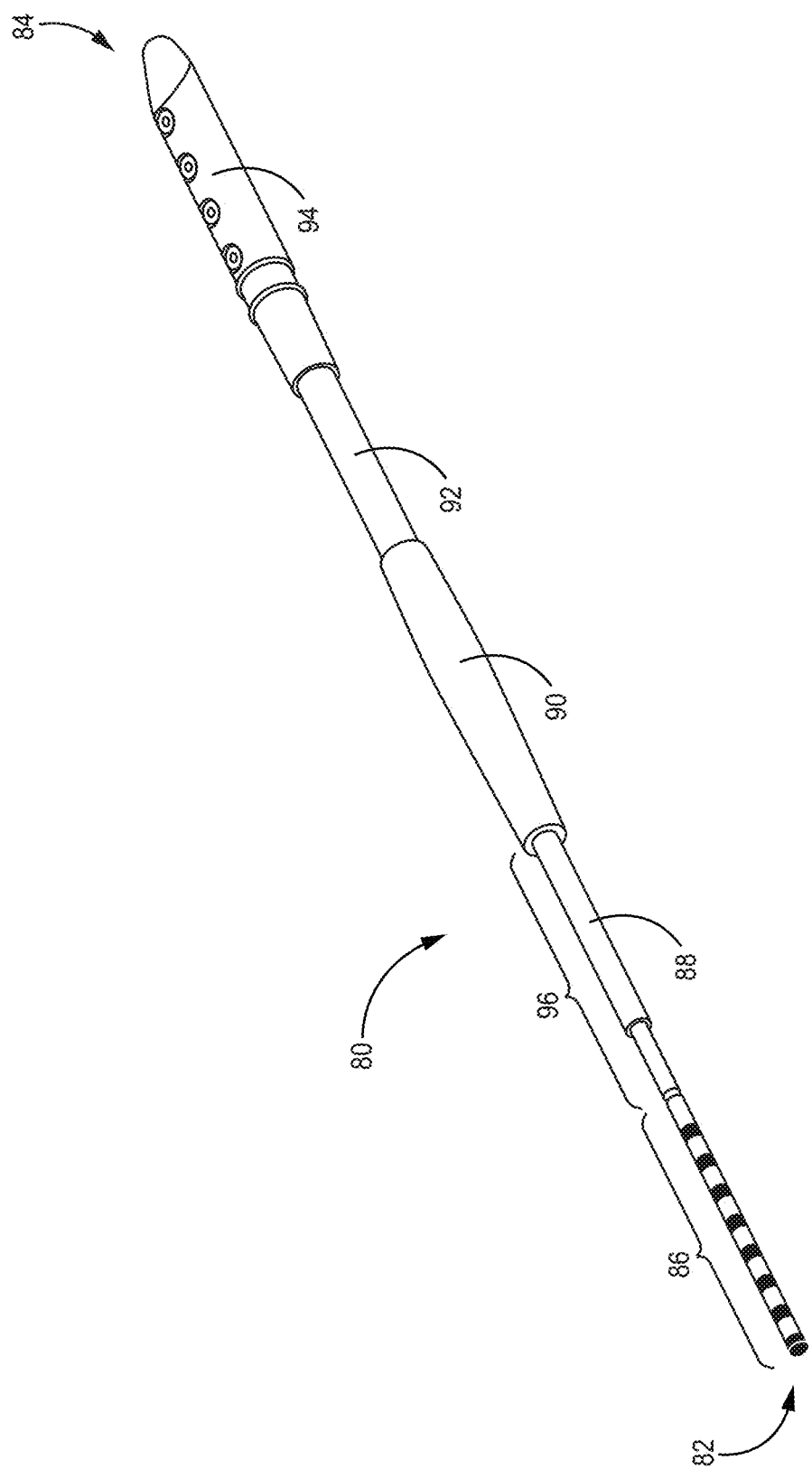
FIG. 4D is a conceptual diagram illustrating a perspective view of an example medical lead extension.

In addition to medical leads, implantable medical leads may include other elongated members used as conduits between electrodes and electrical stimulation devices. FIG. 4D is a conceptual diagram illustrating a perspective view of an example medical lead extension 80. Lead extension 80 includes a distal end 84 and a proximal end 82. Lead extension 80 includes a plurality of contacts 86 at proximal end 82, non-extensible body section 88, a transition 90, an extensible body section 92, and a set screw connector 94 at distal end 54A.

Lead extension may include conductors (not shown) that electrically couple the plurality of contacts 86 to connectors of set screw connector 94. These conductors may be surrounded by a sleeve that includes portions, such as near the plurality of contact 86 and set screw connector 94, in which the conductors are fixed to the sleeve. However, the sleeve may also include unfixed portions 96 in which the conductors are not fixed to the sleeve, such as near non-extensible body section 88. When non-extensible body section 88 is bent, the conductors may move within non-extensible body section 88 to relieve stress created by the bending.

Figure 5A:
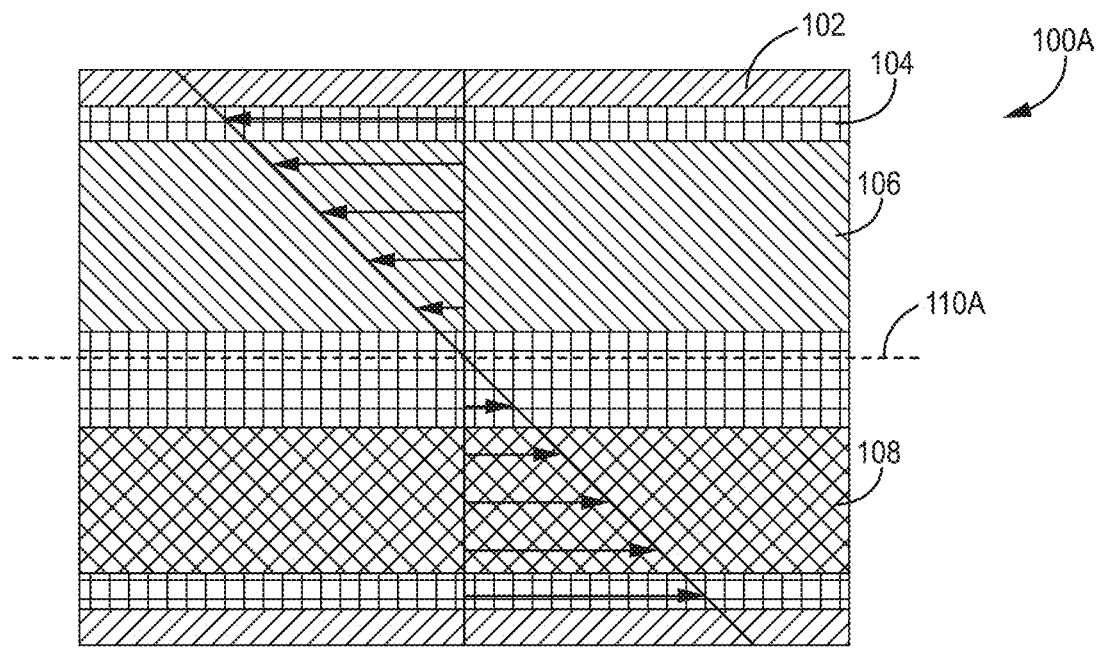
FIG. 5A is a conceptual diagram illustrating conductor strain magnitude in a cross-sectional view of an example implantable medical lead in which a conductor is fixed to a lead body.
Figure 5B:
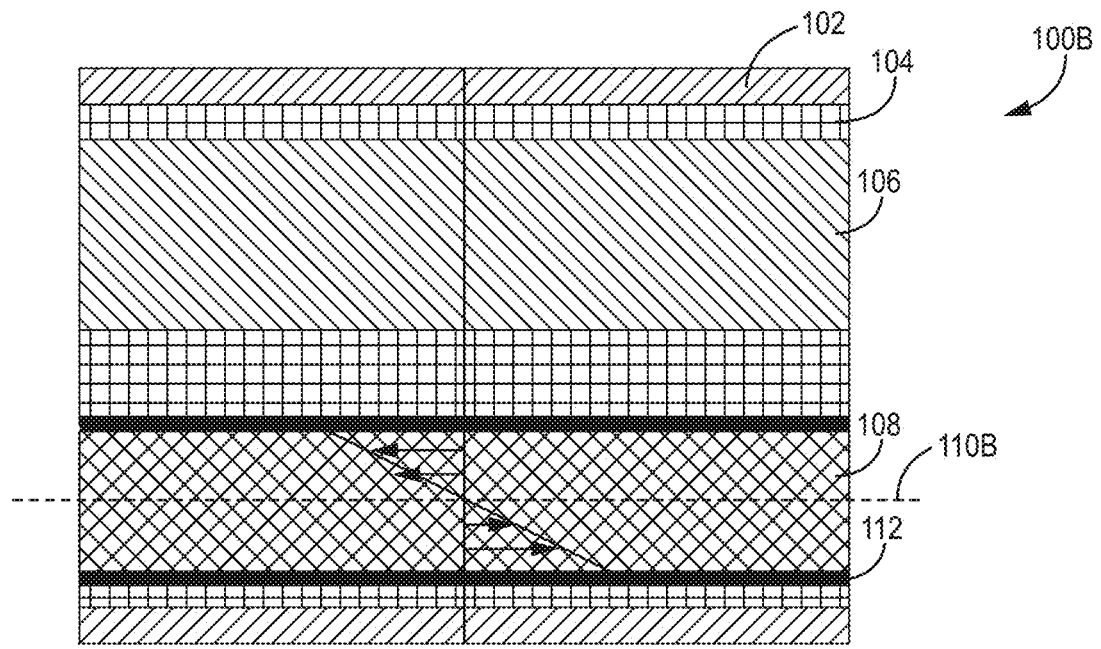
FIG. 5B is a conceptual diagram illustrating conductor strain magnitude in a cross-sectional view of an example implantable medical lead in which a conductor is not fixed to a lead body.

While not being limited to any particular theory, FIGS. 5A-5D illustrate comparative responses to stresses on conductors within implantable medical leads as discussed herein. FIGS. 5A and 5B illustrate a distribution of strains through implantable medical leads having conductors that are fixed and free to move, respectively. FIG. 5A is a conceptual diagram illustrating conductor strain magnitude in a cross-sectional view of an example implantable medical lead 100A in which a conductor 108 is fixed to a lead body. Lead 100A includes a jacket 102, insulative material 104, and a lumen 106 that forms a lead body. When conductor 108 is fixed to insulative material 104 of lead 100A, lead 100A acts as a unified body, such that strains are distributed across a cross-section of lead 100A with a neutral axis 110A, as indicated by arrows left (compressive strains) and right (tensile strains). As such, in the example of FIG. 5A, conductor 108 is offset from neutral axis 110A and therefore subject to a high magnitude of strain that may break conductor 108. For example, strain (ε) may be related to a distance (y) from neutral axis 110A and a radius of curvature (ρ) of a bend as shown in the equation below:

$$\varepsilon = -\frac{y}{\rho}$$

In contrast, FIG. 5B is a conceptual diagram illustrating conductor strain magnitude in a cross-sectional view of an example implantable medical lead 100B in which conductor 108 is not fixed to a lead body. Lead 100B includes jacket 102, insulative material 104, and lumen 106 that forms the lead body. However, in the example of FIG. 5B, a sleeve 112 is positioned around conductor 108, such that sleeve 112 is fixed to insulative material 104 at an outer surface of sleeve 112, but is not fixed to conductor 108 at an inner surface of sleeve 112. When conductor 108 is not fixed to insulative material 104 of lead 100B, conductor 108 acts as a separate body within sleeve 112, such that stresses are distributed across a cross-section of conductor 108 with a neutral axis 110B, rather than across a cross-section of lead 100A with neutral axis 110A. As such, in the example of FIG. 5B, conductor 108 in lead 100B is subject to a lower magnitude of tensile strain than conductor 108 in lead 100A of FIG. 5A.

Figure 5C:
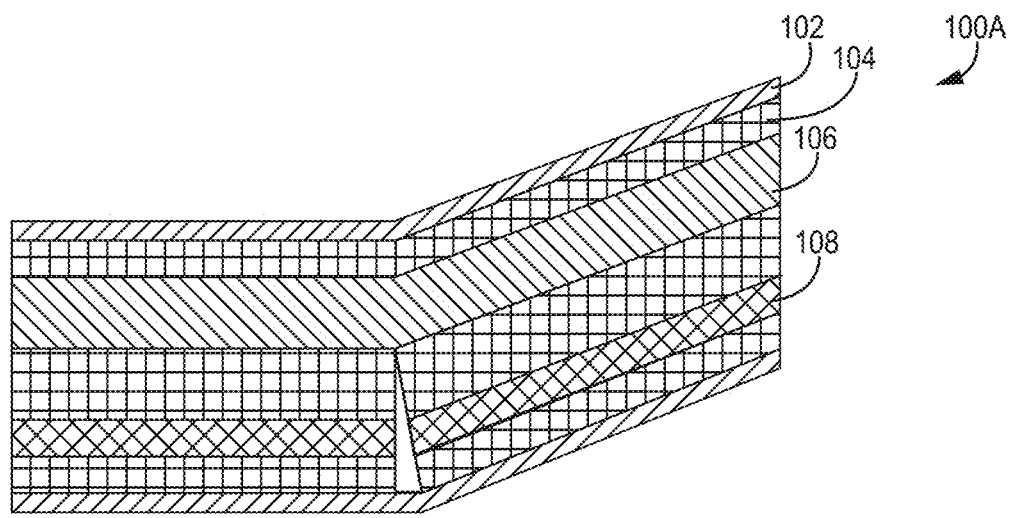
FIG. 5C is a conceptual diagram illustrating a cross-sectional view of a fracture of an example implantable medical lead in which a conductor is fixed to a lead body.
Figure 5D:
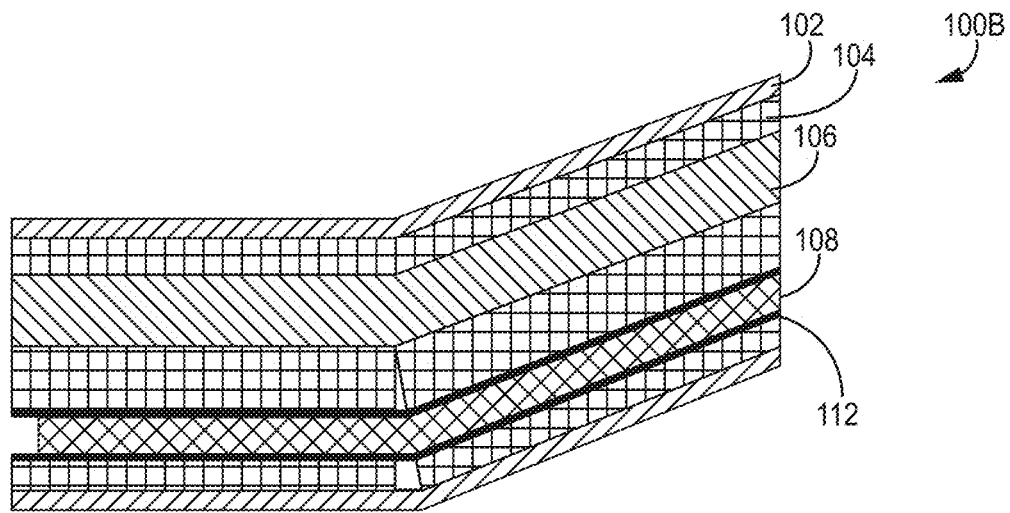
FIG. 5D is a conceptual diagram illustrating a cross-sectional view of a fracture of an example implantable medical lead in which a conductor is not fixed a lead body.

FIGS. 5C and 5D illustrate a response to a crack in implantable medical leads having conductors that are fixed and free to move, respectively. FIG. 5C is a conceptual diagram illustrating a cross-sectional view of a fracture of the example implantable medical lead 100A of FIG. 5A in which conductor 108 is fixed to the lead body. During bending of lead 100A, tensile forces on portions of lead 100A may cause the portions of lead 100A to crack, such as portions of insulative material 104 and conductor 108. FIG. 5D is a conceptual diagram illustrating a cross-sectional view of a fracture of the example implantable medical lead 100B of FIG. 5B in which a conductor is not fixed to a lead body. In contrast to conductor 108 of lead 100A of FIG. 5C, conductor 108 of lead 100B may not be fixed to insulative material 104, such that conductor 108 may move through sleeve 112. As a result, a lower level of tensile strain may be present through conductor 108.

Figure 6:
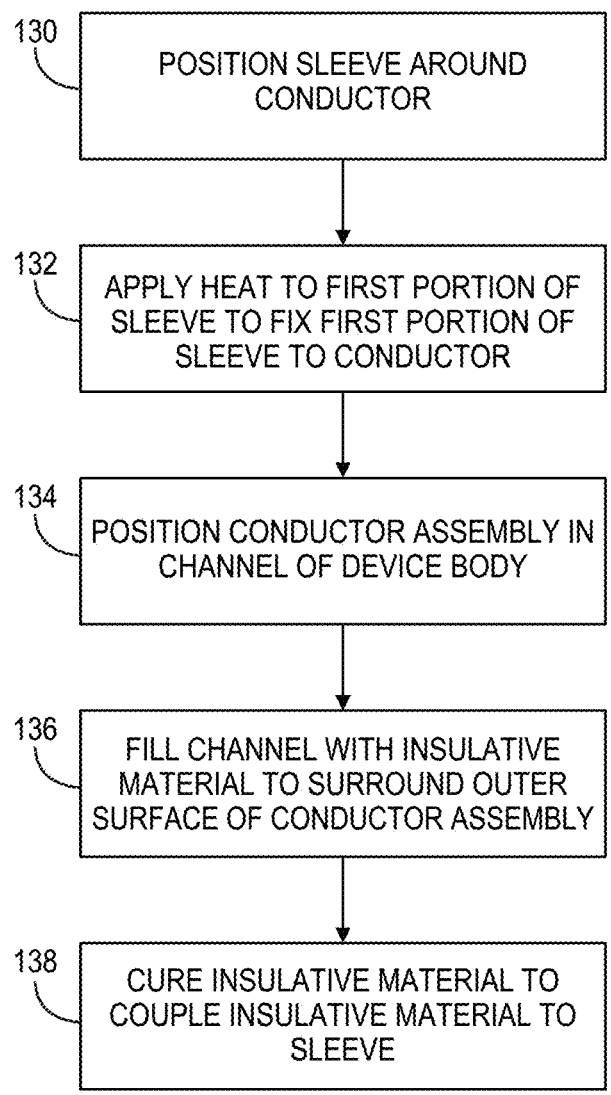
FIG. 6 is a flow diagram of an example technique for manufacturing an implantable medical lead.

FIG. 6 is a flow diagram of an example technique for manufacturing an implantable medical lead, such as lead extension 50 of FIG. 3A. FIG. 6 may only describe a portion of the steps for manufacturing a medical lead having unfixed conductors. Reference may be made to lead extension 50 of FIG. 3A; however, the example technique of FIG. 6 may be used to produce a variety of implantable medical leads. The example technique may include positioning electrical conductor 72A in sleeve 74A (130). In some examples, a length of sleeve 74A is less than a length of conductor 72A. For example, sleeve 74A may be positioned such that an end of conductor 72A is exposed for electrically coupling conductor 72A to electrical connector 56A.

The example technique may include fixing a fixed portion 76A of sleeve 74A to electrical conductor 72A to form conductor assembly 70A (132). A variety of mechanisms may be used to fix fixed portion 76A of sleeve 74A to conductor 72A including, but not limited to, heat treatment, chemical treatment, or any other mechanism that may reduce a size of sleeve 74A such that sleeve 74A exerts a sufficient force on conductor 72A to hold sleeve 74A in place during normal operating conditions. As a result, conductor assembly 70A may include fixed portion 76A that is fixed to conductor 72A and unfixed portion 78A that is not fixed to the electrical conductor. In some examples, sleeve 74A is a heat shrink sleeve. In this example, the technique may include applying heat to an outer surface of sleeve 74A corresponding to fixed portion 76A to shrink fixed portion 76A of sleeve 74A around conductor 72A. In addition to fixing fixed portion 76A of sleeve 74A to conductor 72A, fixed portion 76A may also seal an end of sleeve 74A against conductor 72A. In some examples, conductor assembly 70A may include multiple fixed portions 76A, such that multiple portions of sleeve 74A may be fixed to conductor 72A.

The example technique may include positioning conductor assembly 70 in a channel extending about a longitudinal axis of a preassembled lead body (134). In some examples, the preassembled lead body may include jacket 66 without insulative material 68, such that one or more conductor assemblies 70 may be positioned within jacket 66. In some examples, the preassembled lead body may include insulative material 68 with channels fabricated into insulative material 68, such that conductor assemblies 70 may fit within insulative material 68 without insulative material 68 forming a tight bond with an outside of sleeves 74 of conductor assemblies 70.

In some examples, the example technique may include electrically coupling conductor 72A of conductor assembly 70A to electrical connector 56A. For example, conductor assembly 70A may include a portion at a proximal end of conductor 72A that is not covered by sleeve 74A, such that the bare portion of conductor 72A may be welded to electrical connector 56A.

The example technique may include filling the channel with an insulative material (136). The insulative material surrounds an outer surface of conductor assembly 70A formed by sleeve 74A. In examples in which the channel is formed by jacket 66, the insulative material may fill a volume around lumen 64, conductor 72A, and any other conductors 72 in jacket 66. In some examples, insulative material 68 may fill the channel only to a fill line that is closer to proximal end 52 than an end of sleeve 74A. For example, only a portion of lead extension 50 may include insulative material 68 for structural support. In this design, a proximal end of sleeve 74A have a fixed portion 76A that seals sleeve 74A from insulative material, while a distal end of sleeve 74A may be beyond the fill line of insulative material 68, and may not be sealed. During filling of the channel with the insulative material, fixed portion 76A of sleeve 74A may substantially prevent insulative material from entering into unfixed portion 78A, such that conductor 72A may move within unfixed portion 78A.

The example technique may include curing the insulative material to form insulative material 68 and couple insulative material 68 to sleeve 74 (138). Insulative material 68 may couple to sleeve 74A by contacting or attaching to sleeve 74A, such that sleeve 74A forms an interface with insulative material 68. For example, the insulative material may surround an outer surface of conductor assembly 70A formed by sleeve 74A and chemically and/or mechanically bond with the outer surface of sleeve 74A. The resulting medical lead includes a lead body that is fixed to conductor 72A through fixed portion 76A of sleeve 74A and that is not fixed to conductor 72A through unfixed portion 78A that is not fixed to the conductor 72A.

The above features and techniques are examples. Any suitable techniques may be used to fabricate the structures described herein and may vary based on the particular materials employed for the respective components.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided.

These examples may be combined in any permutation or combination. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Experimental Results

Modeling Sample 1

Figure 7A:
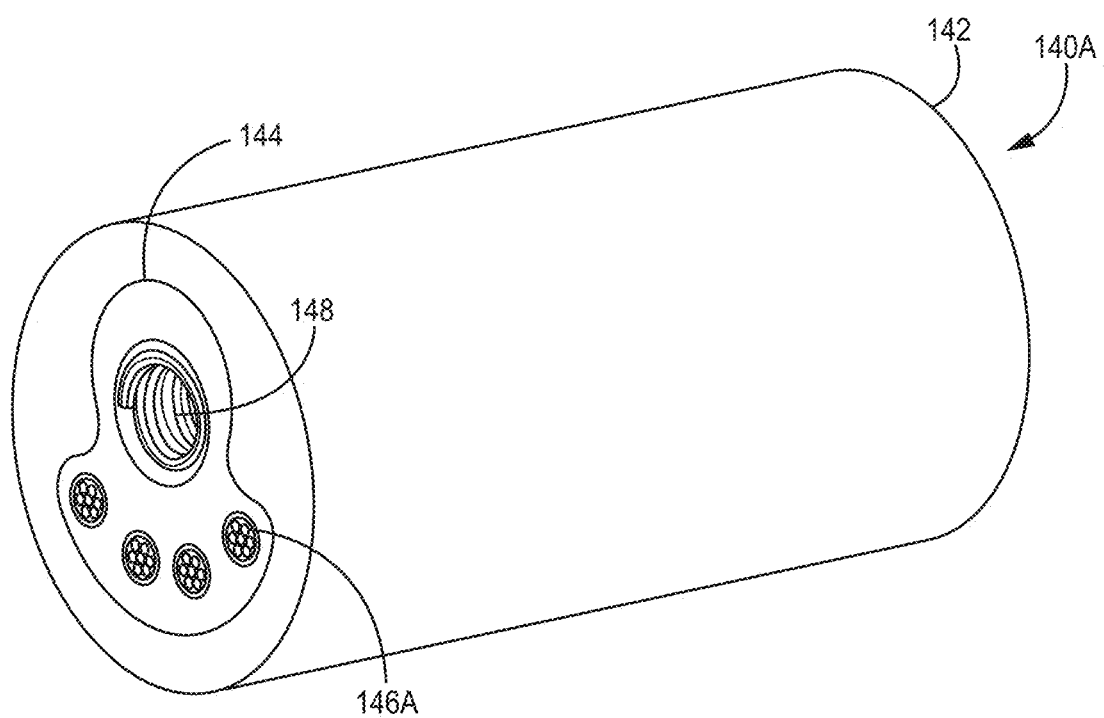
FIG. 7A is a conceptual diagram illustrating a perspective view of a section of an example implantable medical lead.
Figure 7B:
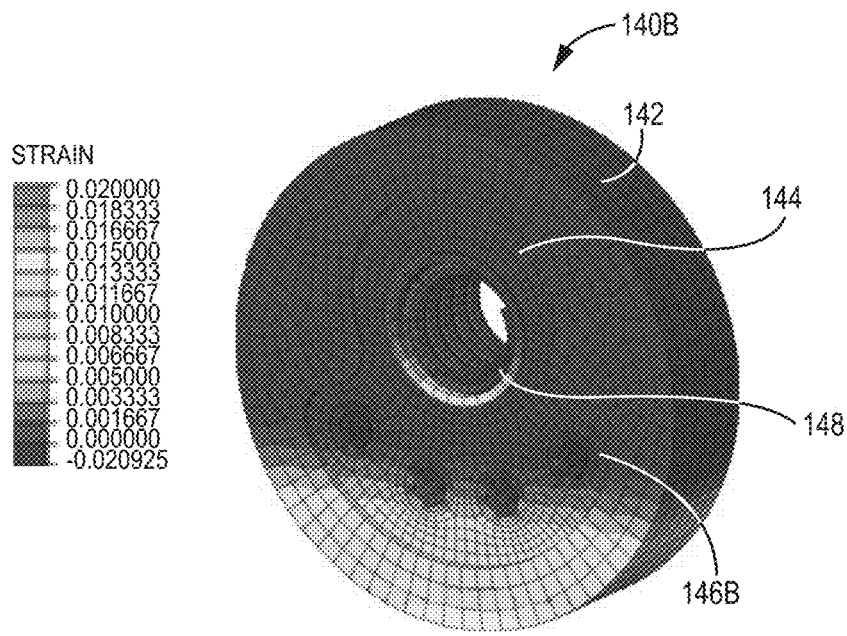
FIG. 7B is a conceptual diagram illustrating conductor strain magnitude in a cross-sectional view of a section of an example implantable medical lead in which conductors are fixed to a lead body.
Figure 7C:
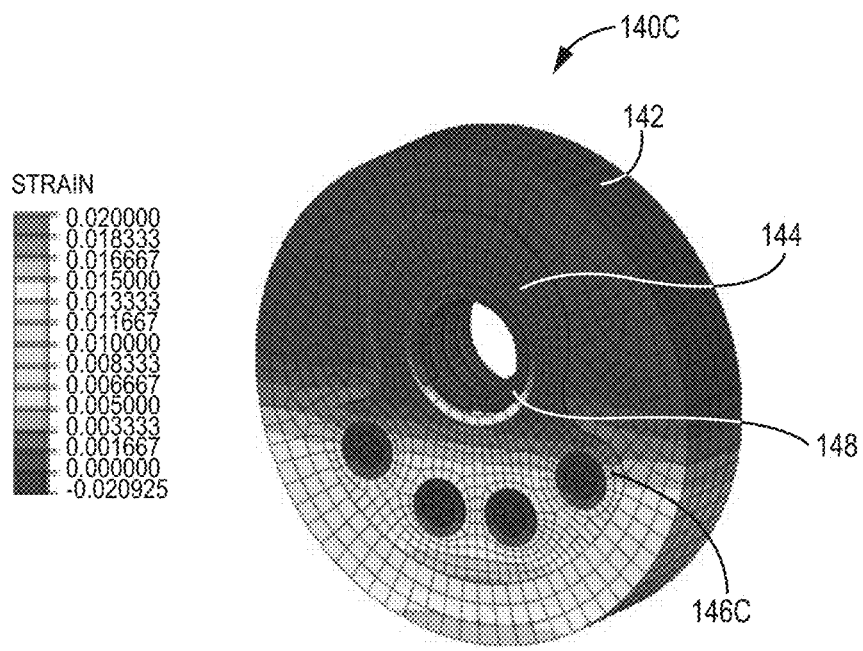
FIG. 7C is a conceptual diagram illustrating conductor strain magnitude in a cross-sectional view of a section of an example implantable medical lead in which conductors are not fixed to a lead body.

FIGS. 7A-7C are diagrams generated from simulations of medical leads as discussed herein that illustrate compressive and tensile stresses on the respective medical leads due to bending away from a neutral axis. For reference, FIG. 7A is a conceptual diagram illustrating a perspective view of a 0.1 inch section of an example medical lead 140A without bending. Medical lead 140A includes a jacket 142, four conductors 146A including a respective cable, a lumen 148 that includes a coil, and a mushroom-shaped epoxy insulative material 144 within jacket 142 and surrounding conductors 146A and lumen 148.

FIG. 7B is a conceptual diagram illustrating conductor strain magnitude in a cross-sectional view of a section of an example implantable medical lead 140B, such as medical lead 140A of FIG. 7A, in which conductors 146B are fixed to insulative material 144. When subjected to a bend about a transverse-axis, medical lead 140B will experience compressive forces on portions at a top of lead 140B, such as a top portion of jacket 142 and a top portion of insulative material 144, and tensile forces on portion at a bottom of lead 140B, such as a bottom portion of jacket 142, a bottom portion of insulative material 144, and conductors 146B. As such, conductors 146B are subjected to similar tensile strains as surrounding insulative material 144, as conductors 146B are fixed to insulative material 144. In contrast, FIG. 7C is a conceptual diagram illustrating conductor strain magnitude in a cross-sectional view of a section of an example implantable medical lead 140C, such as medical lead 140A of FIG. 7A, in which conductors 146C are not fixed to insulative material 144. When subjected to a bend about a transverse-axis, medical lead 140C will experience compressive forces on portions at a top of lead 140C, such as a top portion of jacket 142 and a top portion of insulative material 144, and tensile forces on portions at a bottom of lead 140C, such as a bottom portion of jacket 142 and a bottom portion of insulative material 144. However, conductors 146C are subjected to a much lower magnitude of tensile stresses, as conductors 146C are not fixed to insulative material 144.

Modeling Sample 2

Figure 8A:
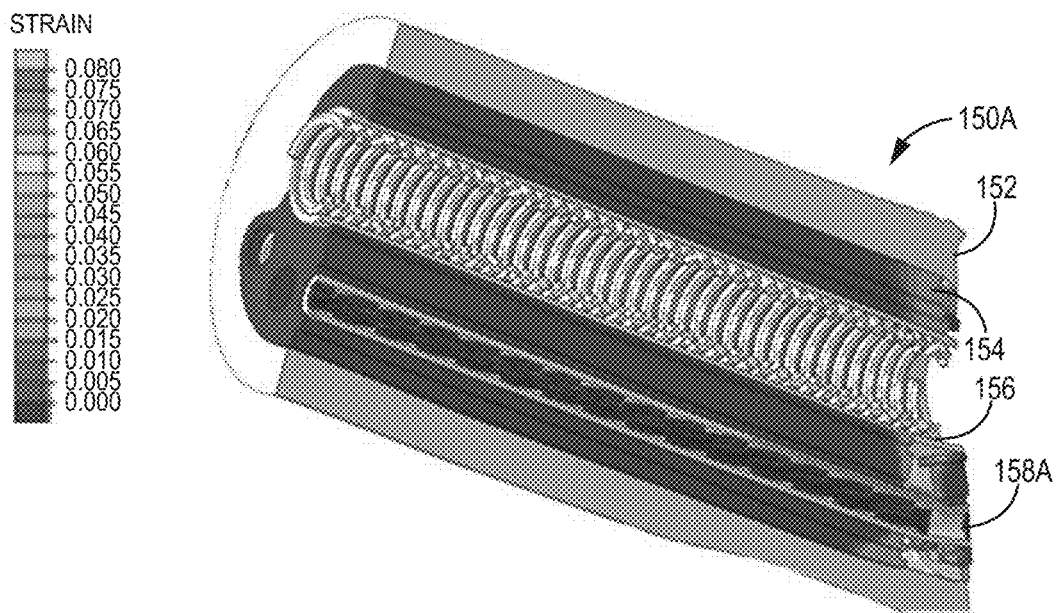
FIG. 8A is a conceptual diagram illustrating a perspective view of a section of an example implantable medical lead in which conductors are fixed to a lead body.
Figure 8B:
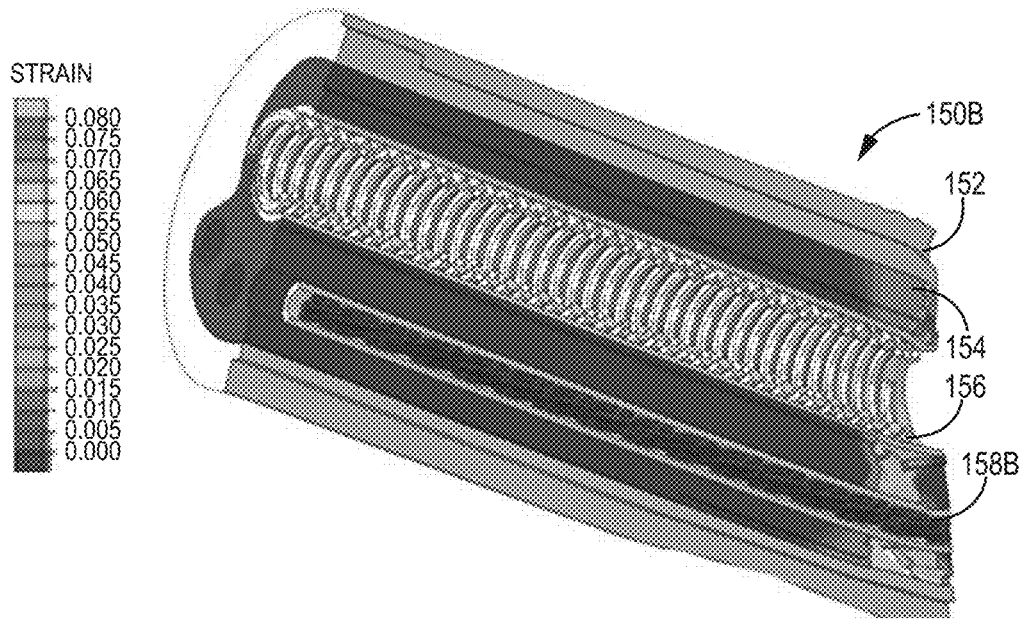
FIG. 8B is a conceptual diagram illustrating a perspective view of a section of an example implantable medical lead in which conductors are not fixed to a lead body.

FIGS. 8A and 8B are diagrams generated from simulations of medical leads as discussed herein that illustrate a response of the medical leads due to bending. FIG. 8A is a conceptual diagram illustrating a perspective view of a section of an example implantable medical lead 150A in which conductor 158A is fixed to insulative material 154 of a lead body. As shown, in FIG. 8A, a bend may break both rigid insulative material 154 and conductor 158A. FIG. 8B is a conceptual diagram illustrating a perspective view of a section of an example implantable medical lead in which conductor 156B is not fixed to insulative material 154 of a lead body. As shown in FIG. 8B, a bend may break insulative material 154, but may not break conductor 158B, as conductor 158B moves within insulative material 154.

Test Methods

Four types of cable samples, representing conductor assemblies as previously described herein, were prepared for testing. In Example 1, a non-shrink-wrapped sleeve was placed over an ETFE insulated cable to simulate portions of a medical lead that are not fixed to an epoxy insulative material. In Example 2, a non-shrink-wrapped sleeve was placed over an ETFE insulated cable to simulate portions of a medical lead that are not fixed to an epoxy insulative material and that have an additional acceleration factor of deeper ETFE embedment within a conductor cable. In Comparative Example 1, an ETFE insulated cable without a non-shrink-wrapped sleeve to simulate portions of a medical lead that are fixed to an epoxy insulative material. In Comparative Example 2, an ETFE insulated cable without a non-shrink-wrapped sleeve to simulate portions of a medical lead that are fixed to an insulating epoxy and that have an additional accelerations factor of deeper ETFE embedment within a conductor cable. Each sample was placed in epoxy within a polyurethane coating, representing a lead body of a medical lead. Three different tests were performed on various samples: a cable removal load test (Example 1, Example 2, Comparative Example 1, and Comparative Example 2); an automated acute header bend test (Example 1, Comparative Example 1, and Comparative Example 2); and an automated acute header bend test followed by chronic header fatigue flex (Example 1 and Comparative Example 1).

Test Method 1—Cable Removal Load Test

A cable removal load test was used to characterize a level of mechanical locking of an ETFE coated cable, representing a conductor at a proximal end of a medical lead, within epoxy, representing a lead body of the medical lead. This cable removal load test may measure a load required to remove the respective cable from a cast of material. The cable removal load test may illustrate differentiation between sample groups with an ability to move within a device body, such as Examples 1 and 2, and sample groups that do not have an ability to move within a device body, such as Comparative Examples 1 and 2, as will be shown below. Further, the cable removal load test may illustrate that an accelerated case that includes a deeper embedment of ETFE into a conductor cable may be successful at increasing mechanical locking in epoxy, as in portions of a conductor assembly in which an ETFE insulated conductor is fixed (or more fixed) to a casting of epoxy, and that a decelerated case that does not include a deeper embedment of ETFE into a conductor cable may be successful at decreasing mechanical locking in epoxy, as in portions of an ETFE insulated conductor assembly in which a conductor is not fixed (or fixed to a lesser extent) to a casting of epoxy. Results for cable removal load test are shown in Table 1 below.

TABLE 1

| Sample Description | Mean Maximum Removal Load (lbf) |
|---|---|
| Example 1 | 0.02171 |
| Example 2 | 0.01340 |
| Comparative Example 1 | 1.4083 |
| Comparative Example 2 | 3.910 |

Figure 9:
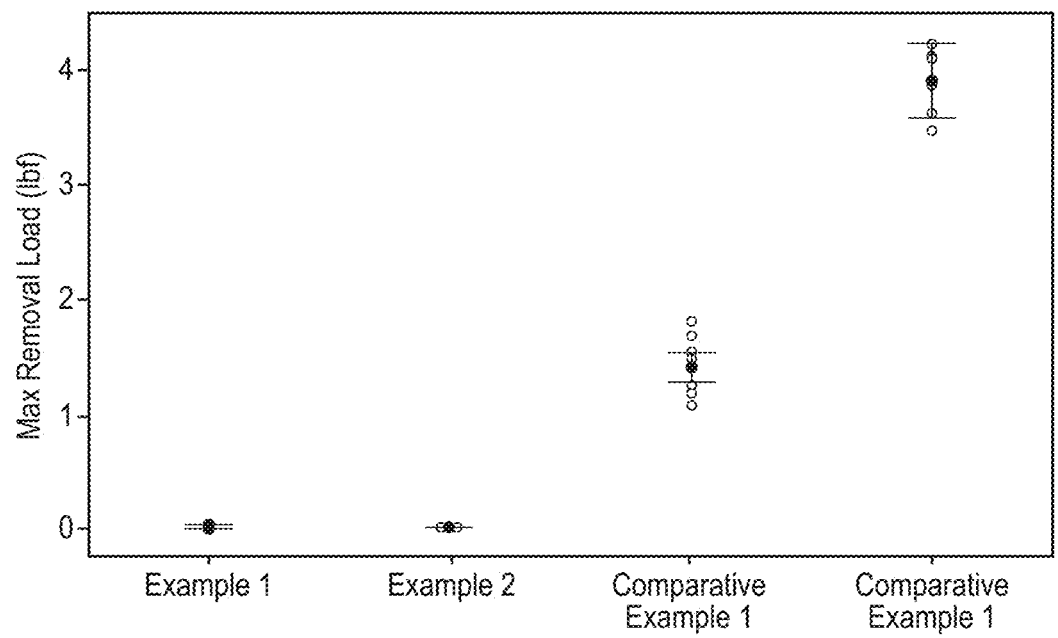
FIG. 9 is a graph of removal load for various example samples.

FIG. 9 is a graph of removal load for Example 1, Example 2, Comparative Example 1, and Comparative Example 2 using the cable removal load test. As shown in FIG. 9, a removal load for non-shrink-wrapped sleeves was significantly lower than removal loads for samples with no sleeve at all. As such, it may be expected that conductors with portions in non-shrink-wrapped sleeves may move within the sleeve when relatively low forces are exerted on the conductors.

Test Method 2—Automated Acute Header Bend Test

An automated acute header bend test was used to detect fractures while simulating a tight bend around a header and controlling cable orientation with respect to the bending neutral axis. In this method, a tight bend is created by bending the extensions around a header while the electrical continuity of the cables within Example 1, Comparative Example 1, and Comparative Example 2 is measured in order to detect a failure. Bending in each direction allows each cable to be tested while it is on the tension side of the neutral bending axis. Results for the automated acute header bend test are shown in Table 2 below.

TABLE 2

| Sample Description | Total Samples | Total Fractured Samples | Fracture Rate |
|---|---|---|---|
| Comparative Example 1 | 8 | 3 | 37.5% |
| Comparative Example 2 | 8 | 7 | 87.5% |
| Example 1 | 7 | 0 | 0% |

As shown in Table 2, fracture may occur in samples with no sleeves in a single cycle. Using heat treatment as an acceleration factor, as in Comparative Example 2, increases the cable fracture rate significantly over the nominal design. This is expected as the acceleration factor increases the mechanical locking of the ETFE coated cables casted in epoxy. In contrast, the non-shrink-wrapped design (Example 1) did not have any cable fractures.

Test Method 3—Automated Acute Header Bend Test Followed by Chronic Header Fatigue Flex An automated acute header bend test followed by a chronic header fatigue flex was performed for Example 1 and Comparative Example 1 to expose an extension to the "90° orientation" tight bend from Test Method 2 followed by the chronic extension to header flex fatigue per the systems specification. This method exposes an extension to a single tight bend per Test Method 2 to understand if that exposure compromises the sample for a fatigue flex per the system requirement. The samples were monitored for electrical continuity for both portions of the test. Results for the automated acute head bend test followed by chronic header fatigue flex are shown in Table 3 below:

TABLE 3

| Sample Description | Total Samples | Total Cable Fractures | Fracture Rate |
|---|---|---|---|
| Comparative Example 1 | 20 | 2 | 10% |
| Example 1 | 7 | 0 | 0% |

Figure 10:
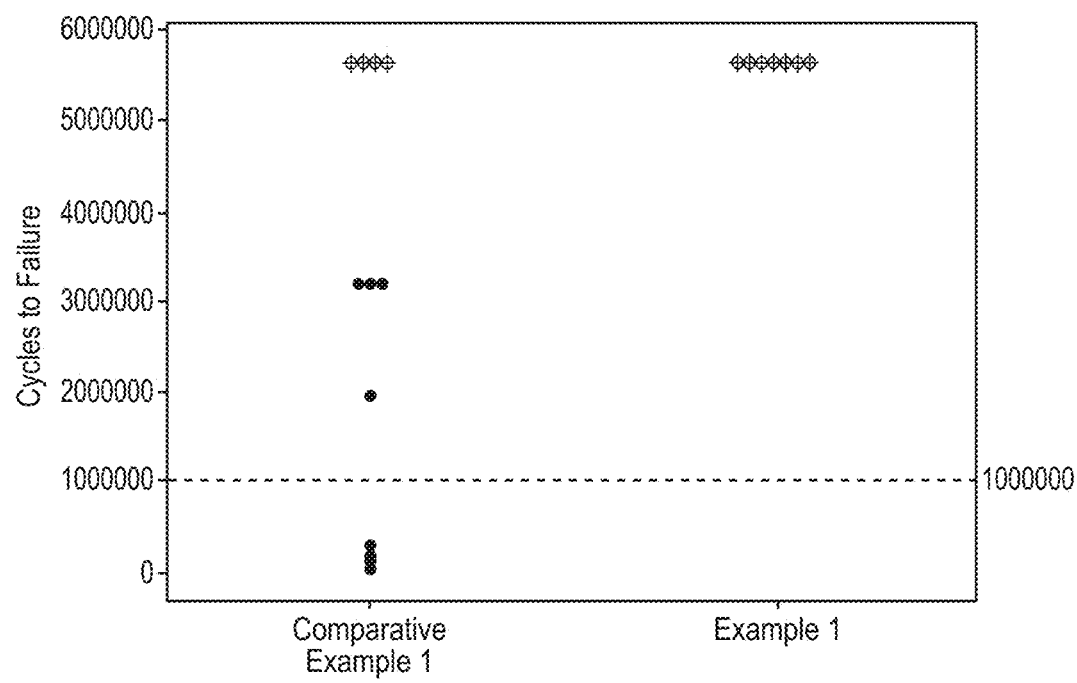
FIG. 10 is a graph of cycles to failure for various example samples.

FIG. 10 is a graph of cycles to failure for Example 1 and Comparative Example 1. Comparative Example 1 was compromised by a tight bend and some samples did not make it to 1 M cycles during the second exposure.

EXAMPLES

Example 1: An implantable medical lead system comprising: a lead body comprising an insulative material, the lead body including a distal end and a proximal end defining a longitudinal axis of the lead body; an electrical connector positioned near the proximal end; an electrical conductor extending about the longitudinal axis of the lead body; a sleeve coupled to the insulative material of the lead body, the sleeve positioned around the electrical conductor, wherein the electrical conductor is electrically coupled to the electrical connector, and wherein the sleeve is not fixed to the electrical conductor.

Example 2: The implantable medical lead system of Example 1, wherein a clearance between the sleeve and the electrical conductor is less than about 125 microns.

Example 3: The implantable medical lead system of Example 1 or 2, wherein an average molecular weight of the insulative material is greater than about 100,000.

Example 4: The implantable medical lead system of any of Examples 1 to 3, wherein the sleeve has a thickness less than about 0.25 mm.

Example 5: The implantable medical lead system of any of Examples 1 to 4, wherein the sleeve has a length greater than about 10 centimeters.

Example 6: The implantable medical lead system of any of Examples 1 to 5, wherein the electrical conductor is configured to axially move relative to the sleeve in response to a flex of the lead body of about 90 degrees at a radius of about five centimeters.

Example 7: The implantable medical lead system of any of Examples 1 to 6, wherein the electrical conductor has an adhesion with the sleeve that corresponds to a mean maximum removal load of the electrical conductor of less than about 0.1 Newtons per meter of the sleeve.

Example 8: The implantable medical lead system of any of Examples 1 to 7, wherein the electrical connector is a first electrical connector, wherein the electrical conductor is a first electrical conductor, wherein the sleeve is a first sleeve, and wherein the medical lead system further comprises: a second electrical connector positioned near the proximal end; a second electrical conductor extending about the longitudinal axis of the lead body; a second sleeve coupled to the insulative material of the lead body, the second sleeve positioned around the second electrical conductor, wherein the second electrical conductor is electrically coupled to the second electrical connector, and wherein the second sleeve is not fixed to the second electrical conductor.

Example 9: The implantable medical lead system of any of Examples 1 to 8, further comprising a medical lead extension that does not include electrodes.

Example 10: The implantable medical lead system of any of Examples 1 to 9, further comprising a plurality of electrodes positioned at the distal end.

Example 11: The implantable medical lead system of any of Examples 1 to 10, further comprising: an electrode at the distal end, wherein the electrode is electrically coupled to the electrical conductor; and an implantable medical device configured to electrically couple to the electrical connector, wherein the implantable medical device is configured to deliver electrical stimulation to the electrode or sense electric signals from the electrode.

Example 12: A method for manufacturing a medical lead comprising: positioning a conductor assembly in a channel extending about a longitudinal axis of a lead body; and filling the channel with an insulative material, the insulative material surrounding an outer surface of the conductor assembly, wherein the lead body includes a distal end and a proximal end defining the longitudinal axis of the lead body, wherein the conductor assembly comprises: an electrical conductor; and a sleeve positioned around the electrical conductor, the sleeve forming the outer surface of the conductor assembly, and wherein the sleeve is not fixed to the electrical conductor.

Example 13: The method of Example 12, wherein a clearance between the sleeve and the electrical conductor is less than about 125 microns.

Example 14: The method of Example 12 or 13, wherein an average molecular weight of the insulative material is greater than about 100,000.

Example 15: The method of any of Examples 12 to 14, wherein the implantable medical lead further comprises an electrical connector positioned near the proximal end, and further comprising electrically coupling the electrical conductor to the electrical connector.

Example 16: The method of any of Examples 12 to 15, further comprising curing the insulative material to couple the insulative material to the sleeve.

Example 17: The method of any of Examples 12 to 16, wherein the sleeve has a length greater than about 2.5 centimeters.

Example 18: The method of any of Examples 12 to 17, wherein a fixed portion of the electrical conductor is proximal to the sleeve.

Example 19: The method of any of Examples 12 to 18, wherein a proximal end of the sleeve is less than about 10 centimeters from the electrical conductor.

Example 20: The method of any of Examples 12 to 19, wherein the conductor assembly is a first conductor assembly, wherein the electrical conductor is a first electrical conductor, wherein the sleeve is a first sleeve, wherein the outer surface is a first outer surface, and wherein the method further comprises: positioning a second conductor assembly in the channel; and filling the channel with the insulative material, the insulative material surrounding a second outer surface of the second conductor assembly, wherein the second conductor assembly comprises: a second electrical conductor; and a second sleeve positioned around the second electrical conductor, the second sleeve forming the second outer surface of the conductor assembly, and wherein the second sleeve is not fixed to the second electrical conductor.

Various aspects of the disclosure have been described. These and other aspects are within the scope of the following claims.

What is claimed is:

1. An implantable medical lead system comprising:
    a lead body comprising an insulative material, the lead body including a distal end and a proximal end defining a longitudinal axis of the lead body;
    an electrical connector positioned near the proximal end;
    an electrical conductor extending about the longitudinal axis of the lead body;
    a tubular sleeve coupled to the insulative material of the lead body, the sleeve positioned around the electrical conductor between the insulative material and the electrical conductor, the tubular sleeve entirely surrounding a circumference of the electrical conductor at the proximal end of the lead body,
    wherein the electrical conductor is electrically coupled to the electrical connector, and
    wherein the tubular sleeve is not fixed to the electrical conductor.

2. The implantable medical lead system of claim 1, wherein a clearance between the tubular sleeve and the electrical conductor is less than 125 microns, and wherein an average molecular weight of the insulative material is greater than 100,000.

3. The implantable medical lead system of claim 1, wherein the tubular sleeve has a thickness less than 0.25 mm.

4. The implantable medical lead system of claim 1, wherein the tubular sleeve has a length greater than 10 centimeters.

5. The implantable medical lead system of claim 1, wherein the electrical conductor is configured to axially move relative to the tubular sleeve in response to a flex of the lead body of 90 degrees at a radius of five centimeters.

6. The implantable medical lead system of claim 1, wherein the electrical conductor has an adhesion with the tubular sleeve that corresponds to a mean maximum removal load of the electrical conductor of less than 0.1 Newtons per meter of the tubular sleeve.

7. The implantable medical lead system of claim 1, wherein the electrical connector is a first electrical connector, wherein the electrical conductor is a first electrical conductor, wherein the tubular sleeve is a first tubular sleeve, and wherein the medical lead system further comprises:
    a second electrical connector positioned near the proximal end;
    a second electrical conductor extending about the longitudinal axis of the lead body;
    a second tubular sleeve coupled to the insulative material of the lead body, the second sleeve positioned around the second electrical conductor between the insulative material and the second electrical conductor, the second tubular sleeve entirely surrounding a circumference of the second electrical conductor at the proximal end of the lead body,
    wherein the second electrical conductor is electrically coupled to the second electrical connector, and
    wherein the second tubular sleeve is not fixed to the second electrical conductor.

8. The implantable medical lead system of claim 1, further comprising a medical lead extension that does not include electrodes.

9. The implantable medical lead system of claim 1, further comprising a plurality of electrodes positioned at the distal end.

10. The implantable medical lead system of claim 1, further comprising:
    an electrode at the distal end, wherein the electrode is electrically coupled to the electrical conductor; and
    an implantable medical device configured to electrically couple to the electrical connector, wherein the implantable medical device is configured to deliver electrical stimulation to the electrode or sense electric signals from the electrode.

11. The implantable medical lead system of claim 1, wherein the electrical conductor further comprises an electrical insulator sheath around a conductive portion of the electrical conductor.

12. A method for manufacturing a medical lead comprising:
    positioning a conductor assembly in a channel extending about a longitudinal axis of a lead body, the conductor assembly comprising an electrical conductor and a tubular sleeve positioned around the electrical conductor, the tubular sleeve forming an outer surface of the conductor assembly; and
    filling the channel with an insulative material, the insulative material surrounding the outer surface of the conductor assembly, and the tubular sleeve positioned between the insulative material and the electrical conductor,
    wherein the lead body includes a distal end and a proximal end defining the longitudinal axis of the lead body,
    wherein the tubular sleeve entirely surrounds a circumference of the electrical conductor at the proximal end of the lead body, and
    wherein the tubular sleeve is not fixed to the electrical conductor.

13. The method of claim 12,
    wherein a clearance between the tubular sleeve and the electrical conductor is less than 125 microns, and
    wherein an average molecular weight of the insulative material is greater than 100,000.

14. The method of claim 12, wherein the implantable medical lead further comprises an electrical connector positioned near the proximal end, and further comprising electrically coupling the electrical conductor to the electrical connector.

15. The method of claim 12, further comprising curing the insulative material to couple the insulative material to the tubular sleeve.

16. The method of claim 12, wherein the tubular sleeve has a length greater than 2.5 centimeters.

17. The method of claim 12, wherein a fixed portion of the electrical conductor is proximal to the tubular sleeve.

18. The method of claim 12, wherein a proximal end of the tubular sleeve is less than 10 centimeters from the electrical conductor.

19. The method of claim 12, wherein the conductor assembly is a first conductor assembly, wherein the electrical conductor is a first electrical conductor, wherein the sleeve is a first tubular sleeve, wherein the outer surface is a first outer surface, and wherein the method further comprises:
    positioning a second conductor assembly in the channel, the second conductor assembly comprising a second electrical conductor and a second tubular sleeve positioned around the electrical conductor, and the second sleeve forming a second outer surface of the second conductor assembly; and
    filling the channel with the insulative material, the insulative material surrounding a second outer surface of the second conductor assembly, and the second sleeve positioned between the insulative material and the second electrical conductor,
    wherein the second tubular sleeve entirely surrounds a circumference of the second electrical conductor at the proximal end of the lead body, and
    wherein the second tubular sleeve is not fixed to the second electrical conductor.

* * * * *